(12) United States Patent
Jackson et al.

(10) Patent No.: US 11,932,695 B2
(45) Date of Patent: Mar. 19, 2024

(54) MODIFIED ANTIBODIES AND RELATED COMPOUNDS, COMPOSITIONS AND METHODS OF USE

(71) Applicant: Sensei Biotherapeutics, Inc., Rockville, MD (US)

(72) Inventors: David Y. Jackson, Belmont, CA (US); Edward Ha, Solano Beach, CA (US)

(73) Assignee: Sensei Biotherapeutics, Inc., Rockville, MD (US)

(*) Notice: Subject to any disclaimer, the term of this patent is extended or adjusted under 35 U.S.C. 154(b) by 0 days.

(21) Appl. No.: 16/903,645

(22) Filed: Jun. 17, 2020

(65) Prior Publication Data

US 2021/0139596 A1 May 13, 2021

Related U.S. Application Data

(63) Continuation of application No. 14/895,896, filed as application No. PCT/US2014/041414 on Jun. 6, 2014, now Pat. No. 10,781,259.

(60) Provisional application No. 61/832,132, filed on Jun. 6, 2013.

(51) Int. Cl.
*C07K 16/28* (2006.01)
*A61K 47/54* (2017.01)

(52) U.S. Cl.
CPC .......... *C07K 16/2863* (2013.01); *A61K 47/54* (2017.08); *A61K 47/545* (2017.08); *C07K 2317/30* (2013.01)

(58) Field of Classification Search
None
See application file for complete search history.

(56) References Cited

U.S. PATENT DOCUMENTS

| | | | |
|---|---|---|---|
| 4,381,195 | A | 4/1983 | Hyzak |
| 4,500,467 | A | 2/1985 | Kubinyi et al. |
| 7,994,135 | B2 | 8/2011 | Doronina et al. |
| 8,389,697 | B2 | 3/2013 | Beria et al. |
| 10,781,259 | B2 | 9/2020 | Jackson et al. |
| 11,229,711 | B2 | 1/2022 | Jackson et al. |
| 2004/0092578 | A1 | 5/2004 | Sheppard et al. |
| 2005/0201964 | A1 | 9/2005 | Malle et al. |
| 2006/0128754 | A1 | 6/2006 | Hoefle et al. |
| 2006/0233794 | A1 | 10/2006 | Law et al. |
| 2009/0175865 | A1 | 7/2009 | Eigenbrot et al. |
| 2011/0021568 | A1 | 1/2011 | Ellman et al. |
| 2011/0085970 | A1 | 4/2011 | Terrett et al. |
| 2012/0190124 | A1 | 7/2012 | Smith et al. |
| 2013/0224228 | A1 | 8/2013 | Jackson et al. |
| 2014/0363454 | A1 | 12/2014 | Jackson et al. |
| 2015/0307551 | A1 | 10/2015 | Doroski et al. |
| 2016/0303247 | A1 | 10/2016 | Jackson et al. |
| 2018/0147294 | A1 | 5/2018 | Jackson et al. |
| 2019/0209704 | A1 | 7/2019 | Jackson et al. |
| 2020/0392108 | A1 | 12/2020 | Jackson et al. |
| 2023/0109312 | A1 | 4/2023 | Jackson et al. |

FOREIGN PATENT DOCUMENTS

| | | |
|---|---|---|
| CA | 2770617 A1 | 2/2011 |
| EP | 2949343 A1 | 12/2015 |
| WO | 2007/034479 A2 | 3/2007 |
| WO | 2011/017249 A1 | 2/2011 |
| WO | 2011/018613 A1 | 2/2011 |
| WO | 2011/036075 A1 | 3/2011 |
| WO | 2013/078377 A1 | 5/2013 |
| WO | 2013/085925 A1 | 6/2013 |
| WO | 2013/121175 A1 | 8/2013 |
| WO | 2014/009774 A1 | 1/2014 |
| WO | 2014/059028 A1 | 4/2014 |
| WO | 2014/114207 A1 | 7/2014 |
| WO | 2014/197866 A1 | 12/2014 |
| WO | 2014/197871 A2 | 12/2014 |
| WO | 2015/004400 A1 | 1/2015 |

OTHER PUBLICATIONS

McKenzie et al. "Development of a bifunctional crosslinking agent with potential for the preparation of immunotoxins" Journal of Protein Chemistry, 1988, vol. 7, pp. 581-592.*
Balan et al., Site-specific PEGylation of protein disulfide bonds using a three-carbon bridge. Bioconjug Chem. Jan.-Feb. 2007;18(1):61-76.
Brocchini et al., PEGylation of native disulfide bonds in proteins. Nat Protoc. 2006;1(5):2241-52.
Castaneda et al., Acid-cleavable thiomaleamic acid linker for homogeneous antibody-drug conjugation. Chem Commun (Camb). Sep. 25, 2013;49(74):8187-9.
Chisholm et al., Regiocontrolled synthesis of the antitumor antibiotic AT2433-A1. J Org Chem. Nov. 3, 2000;65(22):7541-53.
Chudasama et al., Bromopyridazinedione-mediated protein and peptide bioconjugation. Chem Commun (Camb). Aug. 21, 2011;47(31):8781-3.
Filpula, Antibody engineering and modification technologies. Biomol Eng. Jun. 2007;24(2):201-15.
Hudis, Trastuzumab—mechanism of action and use in clinical practice. N Engl J Med. Jul. 5, 2007;357(1):39-51.
Schumacher et al., Homogeneous antibody fragment conjugation by disulfide bridging introduces 'spinostics'. Sci Rep. 2013;3:1525. 8 pages.
Schumacher et al., In situ maleimide bridging of disulfides and a new approach to protein PEGylation. Bioconjug Chem. Feb. 16, 2011;22(2):132-6.
Smith et al., Protein modification, bioconjugation, and disulfide bridging using bromomaleimides. J Am Chem Soc. Feb. 17, 2010;132(6):1960-5.

(Continued)

*Primary Examiner* — Joseph R Kosack
(74) *Attorney, Agent, or Firm* — McCarter & English, LLP; Yelena Margolin

(57) ABSTRACT

Provided herein are modified antibodies, compounds used to make them, and intermediates in their synthesis; compositions; formulations and methods, including methods of treating diseases, disorders or conditions, for example, cancer, in humans.

6 Claims, 13 Drawing Sheets

(56) References Cited

OTHER PUBLICATIONS

International Search Report and Written Opinion for Application No. PCT/US2014/041414, dated Aug. 21, 2014, 9 pages.
Badescu et al., Bridging disulfides for stable and defined antibody drug conjugates. Bioconjug Chem. 2014 Pre-publication version, 13 pages.
Benetti et al., Synthesis of 2,5-Disubstituted Pyrroles and Pyrrolidines by Intramolecular Cyclization of 6-Amino-3-keto Sulfones. Synthesis. 2002;3:331-338.
Del Rosario et al., Sulfhydryl site-specific cross-linking and labeling of monoclonal antibodies by a fluorescent equilibrium transfer alkylation cross-link reagent. Bioconjug Chem. Jan.-Feb. 1990;1(1):51-9.
Doronina et al., Enhanced activity of monomethylauristatin F through monoclonal antibody delivery: effects of linker technology on efficacy and toxicity. Bioconjug Chem. Jan.-Feb. 2006;17(1):114-24.
Ducry et al., Antibody-drug conjugates: linking cytotoxic payloads to monoclonal antibodies. Bioconjug Chem. Jan. 2010;21(1):5-13.
Filigheddu et al., Small Ring Constrained Peptidomimetics. Synthesis of Aziridine Parallel beta-Sheet Mimetics. Tetrahedron Letters. 1998;39:3857-3860.
Fischer, Synthese von Polypeptiden II. Berichte der Deutschen Chemischen Gesellschaft. Wiley-VCH Verlag GmbH & Co. pp. 2486-2511, Jan. 1, 1904.
Fliege et al., Electrophilic Properties of Patulin. Adduct Structures and Reaction Pathways with 4-Bromothiophenol and Other Model Nucleophiles. Chem Res Toxicol. 2000;13:363-372.
Hirao et al., Stereoselective Synthesis of (±)-11-Hydroxy-trans-8-dodecenoic Acid from 10-Undecenoic Acid. J Org Chem. 1985;50:279-281.
King et al., Facile synthesis of maleimide bifunctional linkers. Tetrahedron Letters. Mar. 11, 2002;43(11):1987-1990.
Marculescu et al., Aryloxymaleimides for cysteine modification, disulfide bridging and the dual functionalization of disulfide bonds. Chem Commun (Camb). Jul. 11, 2014;50(54):7139-42.
Palanki et al., Development of a long acting human growth hormone analog suitable for once a week dosing. Bioorg Med Chem Lett. Jan. 15, 2013;23(2):402-6.
Ricart et al., Technology insight: cytotoxic drug immunoconjugates for cancer therapy. Nat Clin Pract Oncol. Apr. 2007;4(4):245-55.
Ryan et al., Tunable reagents for multi-functional bioconjugation: reversible or permanent chemical modification of proteins and peptides by control of maleimide hydrolysis. Chem Commun (Camb). May 21, 2011;47(19):5452-4.
Schumacher et al., Modification of Antibody Disulfide Bonds with Maleimides. Molecular Life Sciences Conference. Sep. 28, 2011. 2 pages.
STN Accession No. 2013:806870, Preparation of cytotoxic pentapeptides and their antibody drug conjugates for treating cancer. 4 pages, (2022).
International Preliminary Report on Patentability for Application No. PCT/US2014/041399, dated Dec. 17, 2015. 11 pages.
International Search Report and Written Opinion for Application No. PCT/US2015/056260, dated Jul. 15, 2016, 25 pages.
International Search Report for Application No. PCT/US2014/041399, dated Oct. 10, 2014. 5 pages.

* cited by examiner

FIG. 3

| | | Chimeric monoclonal antibodies ("-xi-") |
|---|---|---|
| Type | Name Contains | Examples |
| Tumor | "-tuxi-" | bavituximab, brentuximab, cetuximab, siltuximab, rituximab |
| Cardiovascular | "-cixi-" | abciximab, volociximab |
| Immune system | "-lixi-" | basiliximab, clenoliximab, galiximab, gomiliximab, infliximab, keliximab, lumiliximab, priliximab, teneliximab, vapaliximab |
| Melanoma | "-mexi-" | ecromeximab |
| Bacterial | "-baxi-" | pagibaximab |

| | | Humanized monoclonal antibodies ("-zu-") |
|---|---|---|
| Tumor | "-tuzu-" | afutuzumab, alemtuzumab, bevacizumab, bivatuzumab, cantuzumab, citatuzumab, dacetuzumab, elotuzumab, etaracizumab, farletuzumab, gemtuzumab, inotuzumab, labetuzumab, lintuzumab, matuzumab, milatuzumab, nimotuzumab, oportuzumab, pertuzumab, sibrotuzumab, tacatuzumab, tigatuzumab, trastuzumab, tucotuzumab, veltuzumab |
| Immune system | "-lizu-" | *Immunosuppressive*: aselizumab, apolizumab, benralizumab, cedelizumab, certolizumab, daclizumab, eculizumab, efalizumab, epratuzumab, erlizumab, fontolizumab, mepolizumab, natalizumab, ocrelizumab, omalizumab, pascolizumab, pexelizumab, PRO 140, reslizumab, rontalizumab, rovelizumab, ruplizumab, siplizumab, talizumab, teplizumab, tocilizumab, toralizumab, vedolizumab, visilizumab, TGN1412<br>*Non-immunosuppressive*: Ibalizumab |
| Bacterial | "-bazu-" | tefibazumab |
| Cardiovascular | "-cizu-" | alacizumab, bevacizumab/ranibizumab, etaracizumab, tadocizumab |
| Nervous system | "-nezu-"/"-neuzu-" | bapineuzumab, solanezumab, tanezumab |
| Toxin target | "-toxazu-" | urtoxazumab |
| Viral | "-vizu-" | felvizumab, motavizumab, palivizumab |
| Inerleukin | "-kizu-" | lebrikizumab |
| Angiogensis | "-anibizu-" | ranibizumab |

FIG. 3 (cont.)

| | | Fully Human monoclonal antibodies ("-u-") |
|---|---|---|
| Tumor | "-tumu-"/ "-tu-" | adecatumumab, belimumab, cixutumumab, conatumumab, figitumamab, iratumumab, lexatumumab, lucatumumab, mapatumumab, necitumumab, ofatumumab, olaratumab, panitumumab, pritumumab, robatumumab, votumumab, zalutumab |
| Immune system | "-limu-" | Immunosuppression: adalimumab, atorolimumab, fresolimumab, golimumab, lerdelimumab, metelimumab, morolimumab<br>Activation: Ipilimumab, Tremelimumab -- Other: bertilimumab, zanolimumab |
| Bacterial | "-bacu-" | nebacumab, panobacumab, raxibacumab |
| Bone | "-osu-" | denosumab |
| Nervous system | "-neru-" | gantenerumab |
| Musculo-skeletal | "-mulu-" | stamulumab |
| Viral | "-viru-" | exbivirumab, foravirumab, libivirumab, rafivirumab, regavirumab, sevirumab, tuvirumab |
| Interleukin | "-kinu-" | briakinumab, canakinumab, ustekinumab |
| Fungal | "-fungu-" | efungumab |
| Cardiovascular | "-ciru-" | ramucirumab |

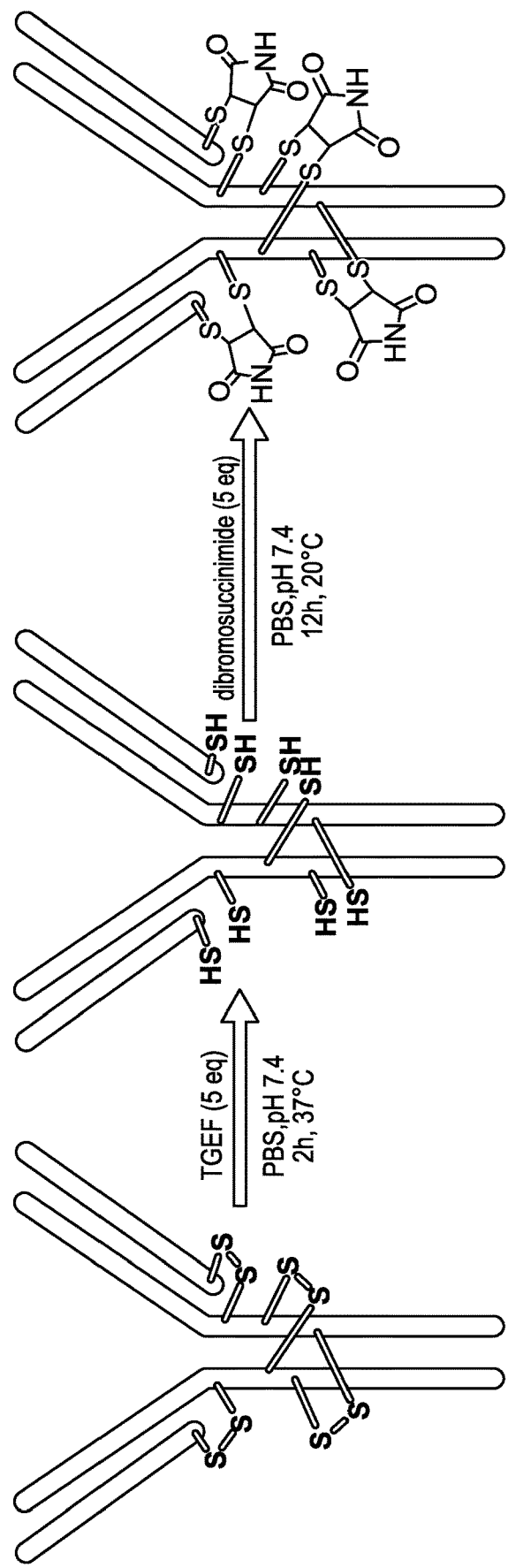

Modified Antibody (4 "staples" per antibody)

Modified Antibody (4 "staples" per antibody)

MODIFIED ANTIBODIES AND RELATED COMPOUNDS, COMPOSITIONS AND METHODS OF USE

CROSS-REFERENCE

This application is a continuation of U.S. patent application Ser. No. 14/895,896, filed on Dec. 3, 2015; which is a 35 U.S.C. § 371 national stage filing of International Application No. PCT/US2014/041414; which claims the benefit of priority of U.S. Provisional Patent Application No. 61/832,132, filed on Jun. 6, 2013. The entire contents of each of the foregoing applications are hereby incorporated herein by reference.

FIELD

Provided herein are modified antibodies, compounds used to make them, and intermediates in their synthesis; compositions; formulations and methods, including methods of treating diseases, disorders or conditions, for example, cancer, in humans.

BACKGROUND

Antibody cysteines can be conjugated to maleimides or other thiol specific functional groups. Antibodies contains multiple interchain disulfide bonds (e.g., 2 between the heavy chains and 2 between heavy and light chains for human IgG1 and IgG4) that covalently bond the heavy and light chains together and contribute to the stability of the antibodies in vivo. These interchain disulfides can be selectively reduced with dithiothreitol, tris(2-carboxyethyl)phosphine, or other mild reducing agents to afford 8 reactive sulfhydryl groups for conjugation.

Schumacher et al., "In Situ Maleimide Bridging of Disulfides and a New Approach to Protein PEGylation", Bioconjugate Chem. 2011, 22, 132-136, disclose the synthesis of 3,4-disubstituted maleimides such as 3,4-bis(2-hydroxyethylsulfanyl)pyrrole-2,5-dione [referred to by Schumacher et al. as "dimercaptoethanolmaleimide"] and 3,4-bis(phenylsulfanyl)pyrrole-2,5-dione ["dithiophenolmaleimide"], and their N-PEGylated derivatives as PEGylating agents for somatostatin, where the substituted maleimide bonds to the two sulfur atoms of the thiols of reduced cysteine-cysteine disulfide bond.

It would be desirable to develop modified antibodies, including those that do not compromise and/or enhance antibody stability.

SUMMARY

The present disclosure provides modified antibodies, compounds used to make them, and intermediates in their synthesis; compositions; formulations and methods, including methods of treating diseases, disorders or conditions, for example, cancer, in humans.

In one aspect, provided herein is a method of modifying an antibody by reacting the antibody with a compound comprising a moiety of the following formula (I):

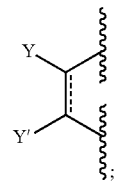

or an enantiomer, diasteriomer, or mixtures thereof;
wherein:
each Y and Y' is independently hydrogen or an electrophilic leaving group that reacts selectively with thiols, provided if one of Y and Y' is hydrogen, the other is the electrophilic leaving group;

the ===== bond represents a single or a double bond; and the symbol ∿∿∿ represents a point of attachment to another group; wherein the antibody is modified by reacting the thiols of two cysteine residues from at least one reduced interchain cysteine-cysteine disulfide with the compound.

In certain embodiments of the method, the compound has the following formula (Ia):

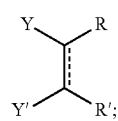

wherein:
each R and R' is independently hydrogen or $C_{1-6}$ alkyl, wherein one or more carbons in the $C_{1-6}$ alkyl are optionally substituted by a group selected from an oxo, a thio, an imine, and a substituted imine; or R and R', together with the two carbons from the single or double bond to which they are attached, form a saturated or unsaturated carbocyclic ring containing from four to seven ring atoms; wherein, excluding the two carbons from the single or double bond, one or more of the ring carbon atoms are optionally replaced by a heteroatom selected from O and N; wherein, excluding the two carbons from the single or double bond, one or more of the ring carbon atoms are optionally substituted by a group selected from an oxo, a thio, an imine, a substituted imine, and a $C_{1-3}$ alkyl; and wherein, if present, the ring nitrogen atom is optionally substituted by a $C_{1-3}$ alkyl.

In certain embodiments of the method, the moiety has one of the following formulas (Ib) and (Ic):

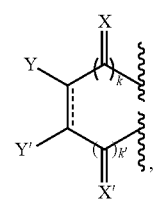

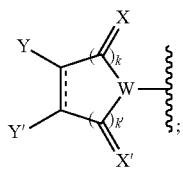
(Ic)

or an enantiomer, diasteriomer, or mixtures thereof;
wherein:
each X and X' is independently absent, O, S, NH, or NR$^1$ wherein R$^1$ is C$_{1-3}$ alkyl; W is —O—, =N—, or =CH—; and
each k and k' is independently an integer of 0, 1, or 2.

In certain embodiments of the method, the compound has one of the following formulas (Id) and (Ie):

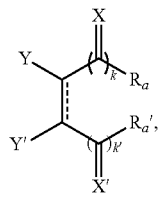
(Id)

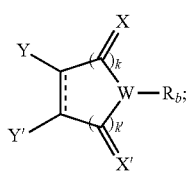
(Ie)

wherein:
each R$_a$, R$_{a'}$ and R$_b$ is independently hydrogen, C$_{1-3}$ alkyl, or absent.

In certain embodiments of the method, the ===== bond represents a single bond.

In certain embodiments of the method, each Y and Y' is independently selected from the group consisting of a halo, a substituted thiol, and a substituted sulfonate. In certain embodiments, each Y and Y' is independently selected from the group consisting of chloro, bromo, fluoro, and iodo. In certain embodiments, each Y and Y' is independently selected from an optionally substituted thiophenyl, an optionally substituted thionaphthyl, an optionally substituted thiopyridyl, an optionally substituted isoquinoline, and an optionally substituted phenylsulfonate.

In certain embodiments of the method, each Y and Y' is independently selected from the group consisting of:

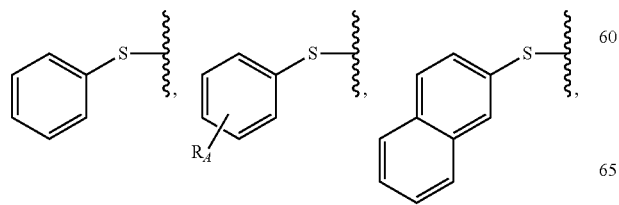

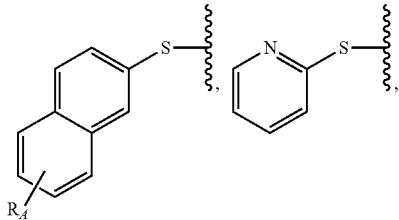

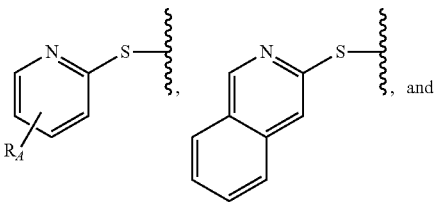
, and

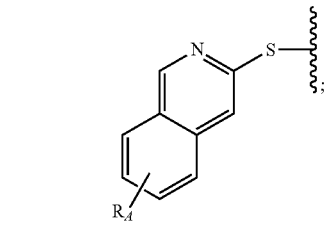

wherein
R$_A$ is selected from the group consisting of hydroxyl, amino, nitro, cyano, chloro, bromo, fluoro, iodo, oxo, carboxyl, C$_{1-6}$ alkoxycarbonyl, C$_{1-6}$ alkyl, C$_{2-6}$ alkenyl, and C$_{1-6}$ alkoxy.

In certain embodiments of the method, each Y and Y' is independently selected from the group consisting of:

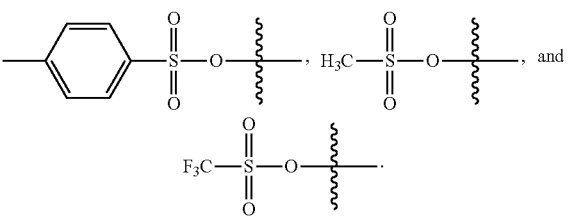

In another aspect, provided herein is a modified antibody of the following formula (II):

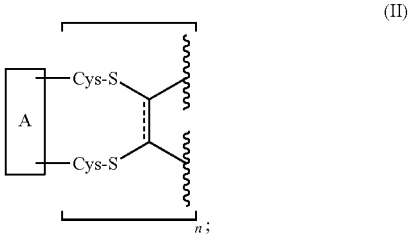
(II)

wherein:
A is an antibody or antibody fragment;
the two depicted cysteine residues are from at least one reduced interchain cysteine-cysteine disulfide bond in A;
n is an integer from 1 to 13;
the ===== bond represents a single or a double bond; and the symbol ⁓⁓⁓ represents a point of attachment to another group.

In certain embodiments, the modified antibody has the following formula (lla):

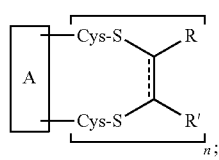

(IIa)

wherein:
each R and R' is independently hydrogen or $C_{1-6}$ alkyl, wherein one or more carbons in the $C_{1-6}$ alkyl are optionally substituted by a group selected from an oxo, a thio, an imine, and a substituted imine; or
R and R', together with the two carbons from the single or double bond to which they are attached, form a saturated or unsaturated carbocyclic ring containing from four to seven ring atoms; wherein, excluding the two carbons from the single or double bond, one or more of the ring carbon atoms are optionally replaced by a heteroatom selected from O and N; wherein, excluding the two carbons from the single or double bond, one or more of the ring carbon atoms are optionally substituted by a group selected from an oxo, a thio, an imine, a substituted imine, and a $C_{1-3}$ alkyl; and wherein, if present, the ring nitrogen atom is optionally substituted by a $C_{1-3}$ alkyl.

In certain embodiments, the modified antibody has one of the following formulas (llb) and (llc):

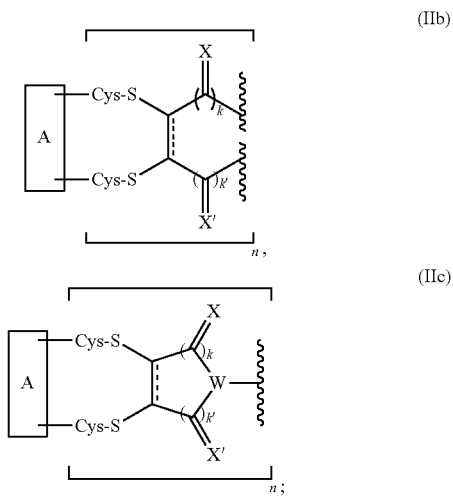

wherein:
each X and X' is independently absent, O, S, NH, or $NR^1$ wherein $R^1$ is $C_{1-3}$ alkyl; W is —O—, =N—, or =CH—; and
each k and k' is independently an integer of 0, 1, or 2.

In certain embodiments, the modified antibody has one of the following formulas (lld) and (lle):

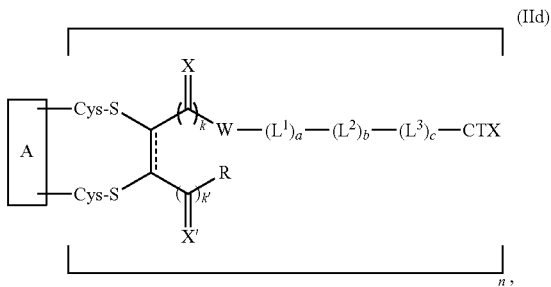

wherein:
each $R_a$, $R_a'$ and $R_b$ is independently hydrogen, $C_{1-3}$ salkyl, or absent.

In certain embodiments of the modified antibody, the ===== bond represents a single bond.

In certain embodiments of the modified antibody, A is an antibody that is specific to a cancer antigen. In certain embodiments, A is selected from the group consisting of alemtuzumab, bevacizumab, brentuximab, cetuximab, gemtuzumab, ipilimumab, ofatumumab, panitumumab, rituximab, tositumomab, inotuzumab, glembatumumab, lovortuzumab and trastuzumab. Additional antibodies include adecatumumab, afutuzumab, bavituximab, belimumab, bivatuzumab, cantuzumab, citatuzumab, cixutumumab, conatumumab, dacetuzumab, elotuzumab, etaracizumab, farletuzumab, figitumumab, iratumumab, labetuzumab, lexatumumab, lintuzumab, lucatumumab, mapatumumab, matuzumab, milatuzumab, necitumumab, nimotuzumab, olaratumab, oportuzumab, pertuzumab, pritumumab, ranibizumab, robatumumab, sibrotuzumab, siltuximab, tacatuzumab, tigatuzumab, tucotuzumab, veltuzumab votumumab, and zalutumumab.

In another aspect, provided herein is an antibody or a formulation thereof obtainable by the methods disclosed herein.

In another aspect, provided herein is a process, which comprises:
(i) reducing one or more interchain cysteine-cysteine disulfide bonds in an antibody with a reducing agent; and
(ii) reacting the free thiol groups from the one or more reduced interchain cysteine-cysteine disulfide bonds with a compound disclosed herein, thus producing a modified antibody.

In certain embodiments of the process, cysteine-cysteine disulfide bonds are reduced (e.g., 1 to 13 interchain disulfide bonds for IgG1, IgG2, IgG3, and/or IgG4). In certain embodiments of the process, for example, for IgG 1, 1 to 4 interchain cysteinecysteine disulfide bonds are reduced.

In certain embodiments of the process, the reducing agent is dithiothreitol (DTT) or tris(2 carboxyethyl)phosphine (TCEP).

In another aspect, provided herein is a pharmaceutical formulation comprising a modified antibody disclosed herein.

In another aspect, provided herein is a method of treating a cancer by administering to a human suffering therefrom a prophylactic or therapeutically effective amount of a pharmaceutical formulation comprising a modified antibody disclosed herein.

BRIEF DESCRIPTION OF THE DRAWINGS

FIG. 3: List of Antibodies in Clinical Trials
FIG. 4: Bifunctional Linkers for Improving Antibody Stability

DETAILED DESCRIPTION

The present disclosure provides modified antibodies, compounds used to make them, and intermediates in their synthesis; compositions; formulations and methods, including methods of treating diseases, disorders or conditions, for example, cancer, in humans. For example, the present disclosure provides modified antibodies and methods of preparing the modified antibodies, for example, by reacting the two thiol groups from at least one reduced interchain disulfide bond with a compound disclosed herein. Such chemically modified antibodies include those that do not compromise and/or enhance antibody stability and are useful in compositions and formulations, and in methods for treating diseases, disorders or conditions in humans.

Definitions

Figure 1:
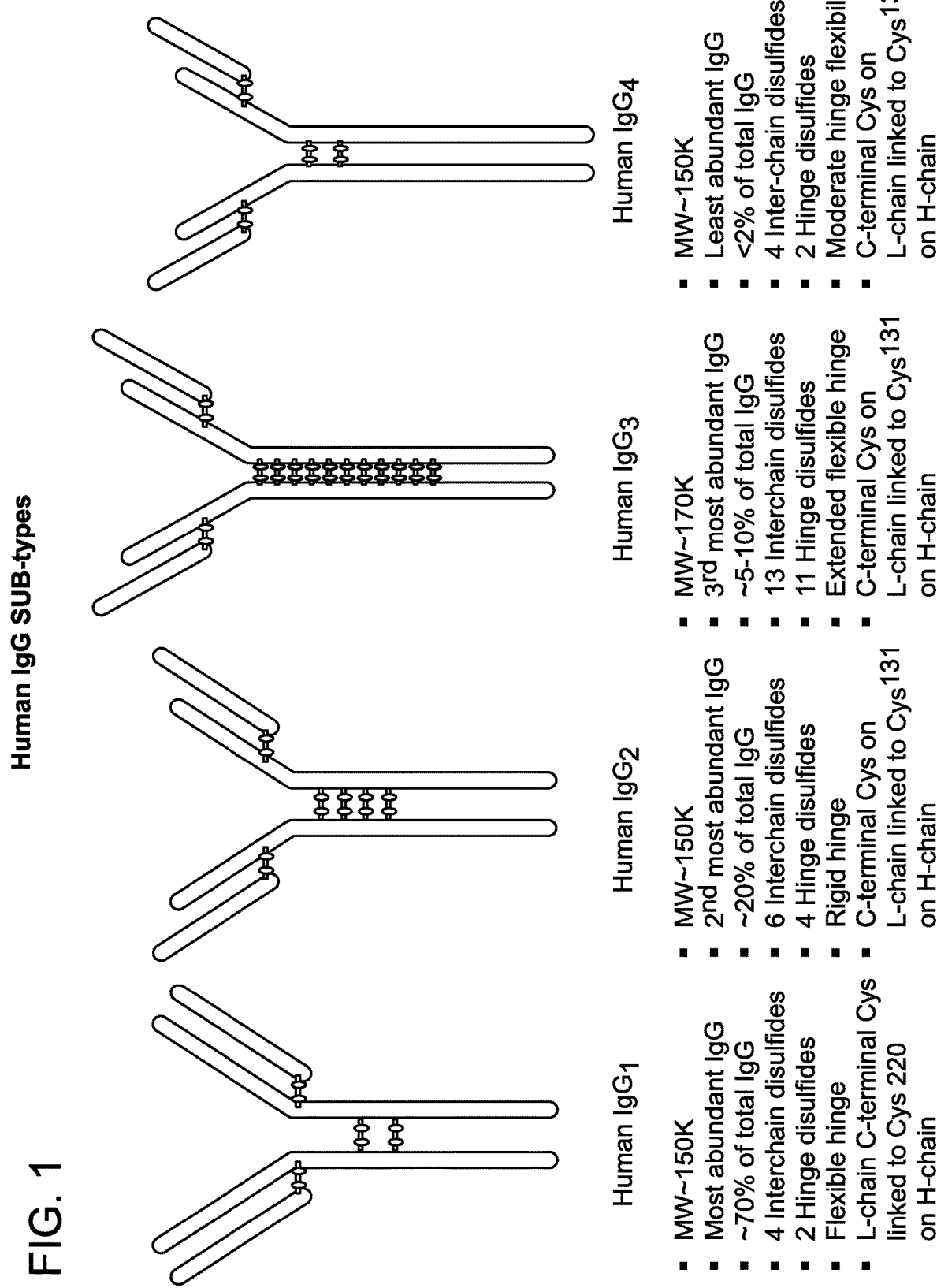
FIG. 1: Human IgG Sub-types
Figure 2:
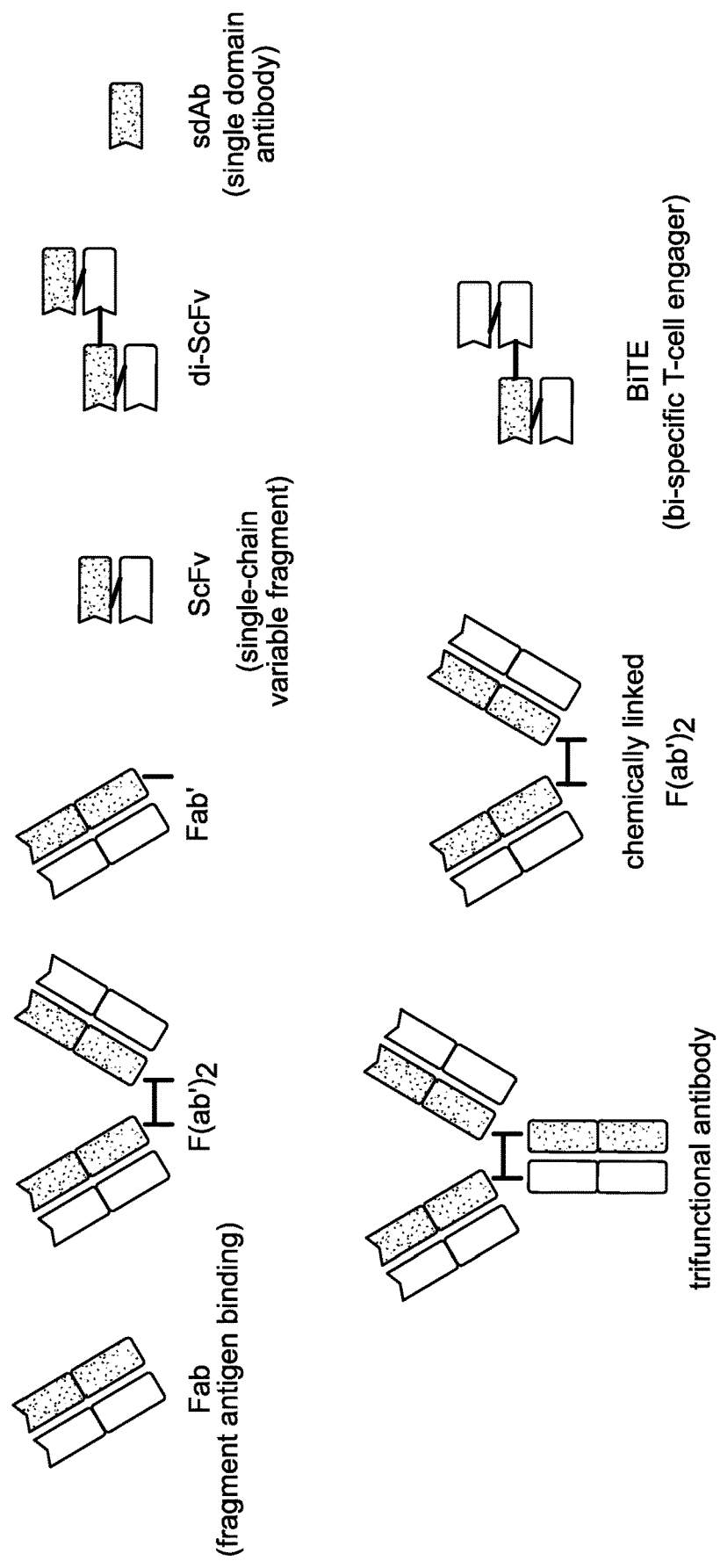
FIG. 2: Forms of Antibodies and Antibody Fragments

An "antibody," also known as an immunoglobulin, is a large Y-shaped protein that binds to an antigen. Antibodies are used by the immune system to identify and neutralize foreign objects such as bacteria and viruses. The antibody recognizes a unique part of the antigen, because each tip of the "Y" of the antibody contains a site that is specific to a site on an antigen, allowing these two structures to bind with precision. An antibody may consist of four polypeptide chains, two heavy chains and two light chains connected by interchain cysteine disulfide bonds (see, e.g., FIG. 1). A "monoclonal antibody" is a monospecific antibody where all the antibody molecules are identical because they are made by identical immune cells that are all clones of a unique parent cell. Initially, monoclonal antibodies are typically prepared by fusing myeloma cells with the spleen cells from a mouse (or B-cells from a rabbit) that has been immunized with the desired antigen, then purifying the resulting hybridomas by such techniques as affinity purification. Recombinant monoclonal antibodies are prepared in viruses or yeast cells rather than in mice, through technologies referred to as repertoire cloning or phage display/yeast display, the cloning of immunoglobulin gene segments to create libraries of antibodies with slightly different amino acid sequences from which antibodies with desired specificities may be obtained. The resulting antibodies may be prepared on a large scale by fermentation. "Chimeric" or "humanized" antibodies are antibodies containing a combination of the original (usually mouse) and human DNA sequences used in the recombinant process, such as those in which mouse DNA encoding the binding portion of a monoclonal antibody is merged with human antibody-producing DNA to yield a partially-mouse, partially-human monoclonal antibody. Full-humanized antibodies are produced using transgenic mice (engineered to produce human antibodies) or phage display libraries. Antibodies (Abs) and "immunoglobulins" (lgs) are glycoproteins having similar structural characteristics. While antibodies exhibit binding specificity to a specific antigen, immunoglobulins include both antibodies and other antibody-like molecules which generally lack antigen specificity. Polypeptides of antibody-like molecules are produced at low levels by the lymph system and at increased levels by myelomas. The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity). Forms of antibodies and antibody fragments are shown schematically in FIG. 2. These antibodies may also include certain antibody fragments. An antibody can be chimeric, human, humanized and/or affinity matured. Exemplary antibodies are shown in FIG. 3. Antibodies of particular interest are those that are specific to cancer antigens, are non-immunogenic, have low toxicity, and are readily internalized by cancer cells; and suitable antibodies include alemtuzumab, bevacizumab, brentuximab, cetuximab, gemtuzumab, ipilimumab, ofatumumab, panitumumab, rituximab, tositumomab, inotuzumab, glembatumumab, lovortuzumab and trastuzumab. Additional antibodies include adecatumumab, afutuzumab, bavituximab, belimumab, bivatuzumab, cantuzumab, citatuzumab, cixutumumab, conatumumab, dacetuzumab, elotuzumab, etaracizumab, farletuzumab, figitumumab, iratumumab, labetuzumab, lexatumumab, lintuzumab, lucatumumab, mapatumumab, matuzumab, milatuzumab, necitumumab, nimotuzumab, olaratumab, oportuzumab, pertuzumab, pritumumab, ranibizumab, robatumumab, sibrotuzumab, siltuximab, tacatuzumab, tigatuzumab, tucotuzumab, veltuzumab votumumab, and zalutumumab.

The terms "full length antibody," "intact antibody" and "whole antibody" are used herein interchangeably to refer to an antibody in its substantially intact form, and are not antibody fragments as defined below. The terms particularly refer to an antibody with heavy chains that contain the Fc region.

"Antibody fragments" comprise only a portion of an intact antibody, wherein the portion retains at least one, two, three and as many as most or all of the functions normally associated with that portion when present in an intact antibody. In one aspect, an antibody fragment comprises an antigen binding site of the intact antibody and thus retains the ability to bind antigen. In another aspect, an antibody fragment, such as an antibody fragment that comprises the Fc region, retains at least one of the biological functions normally associated with the Fc region when present in an intact antibody. Such functions may include FcRn binding, antibody half life modulation, ADCC function and complement binding. In another aspect, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "monoclonal antibody," as used herein, refers to an antibody obtained from a population of substantially homogeneous antibodies, e.g., the individual antibodies comprising the population are identical except for possible mutations, e.g., naturally occurring mutations, that may be present in minor amounts. The modifier term "monoclonal" indicates the character of the antibody as not being a mixture of discrete antibodies. In certain aspects, such a monoclonal antibody may include an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In addition to their specificity, monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. (See, Kohler et al., Nature, 256: 495 (1975); Harlow et al., Antibodies: A Laboratory Manual, (Cold Spring Harbor Laboratory Press, 2.sup.nd ed. 1988); Hammerling et al., in: Monoclonal Antibodies and T-Cell Hybridomas 563681 (Elsevier, N.Y., 1981)), recombinant DNA methods (see, e.g., U.S. Pat. No. 4,816,567), and technologies for producing human or human-like antibodies in animals that have parts or all of the human immunoglobulin loci or genes encoding human immunoglobulin sequences (see, WO98/24893; WO96/34096; WO96/33735 and WO91/10741). The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567). "Humanized" forms of non-human (e.g., murine) antibodies are chimeric antibodies that contain minimal sequence derived from non-human immunoglobulin. In one aspect, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In another aspect, framework region (FR) residues of the human immunoglobulin are replaced by corresponding non-human residues. In general, a humanized antibody will comprise substantially all of at least one, and typically two, variable domains, in which all or substantially all of the hypervariable loops correspond to those of a non-human immunoglobulin, and all or substantially all the FRs are those of a human immunoglobulin sequence. The humanized antibody may comprise at least a portion of an immunoglobulin constant region (Fc), typically that of a human immunoglobulin. See Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Framework" or "FR" residues are those variable domain residues other than the hypervariable region residues. "Fc receptor" or "FcR" is a receptor that binds to the Fc region of an antibody. In certain embodiments, an FcR is a native human FcR. In one aspect, an FcR is one which binds an IgG antibody (a gamma receptor) and includes receptors of the FcERI, FcERII and FcERIII subclasses. (See Dacron, Annu. Rev. Immunol. 15:203-234 (1997)).

An "antibody-drug conjugate" (ADC) is an antibody that is conjugated to one or more cytotoxins, through one or more linkers. The antibody is typically a monoclonal antibody specific to a therapeutic target such as a cancer antigen.

A "cytotoxic agent" or "cytotoxin" is a molecule that has a cytotoxic effect on cells (e.g., when released within a cancer cell, is toxic to that cell).

The term "linker," as used herein, refers to a group of atoms used to connect interconnecting moieties, for example, between an antibody and one or more cytotoxins in an ADC.

The term "polyether," as used herein, refers to a polymer of alkylene that contains at least one ether group, for example, polyoxyalkylene.

The term "polyethylene glycol" (PEG), as used herein, refers to a polymer of ethylene oxide having repeat units of —(CH$_2$CH$_2$—O)—.

The term "PEGylated linker," as used herein, refers to a linker comprising PEG. Examples of linkers include, for example, repeating units of —(CH$_2$CH$_2$O)—, (CH$_2$CH$_2$O) CH$_2$CH$_2$—, —CH$_2$CH$_2$—(CH$_2$CH$_2$O)—, etc.

The term "alkyl," as used herein, means a straight, branched chain, or cyclic (in this case, it would also be known as "cycloalkyl") hydrocarbon containing from 1-10 carbon atoms. Examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl. In certain embodiments, alkyl groups are optionally substituted.

The term "$C_{1-10}$ alkyl," as used herein, means a straight, branched chain, or cyclic (in this case, it would also be known as "cycloalkyl") hydrocarbon containing from 1-10 carbon atoms.

The term "$C_{1-6}$ alkyl," as used herein, means a straight, branched chain, or cyclic (in this case, it would also be known as "cycloalkyl") hydrocarbon containing from 1-6 carbon atoms.

The term "$C_{1-3}$ alkyl," as used herein, means a straight or branched chain hydrocarbon containing from 1-3 carbon atoms.

The term "alkenyl," as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (e.g., an alkenylene group). In some embodiments, alkenyl groups are optionally substituted. Examples of alkenyl include, but are not limited to, ethenyl, 2-propenyl, 2-methyl-2-propenyl, 3-butenyl, 4-pentenyl, 5-hexenyl, 2-heptenyl, and 2-methyl-1-heptenyl. In certain embodiments, alkenyl groups are optionally substituted.

The term "alkoxy," as used herein, means an alkyl group, as defined herein, appended to the parent molecular moiety through an oxygen atom. Examples of alkoxy include, but are not limited to, methoxy, ethoxy, propoxy, 2-propoxy, butoxy, tert-butoxy, pentyloxy, and hexyloxy.

The term "$C_{2-6}$ alkenyl," as used herein, means a straight, branched chain, or cyclic (in this case, it would also be known as "cycloalkyl") hydrocarbon containing from 2-6 carbon atoms and at least one carbon-carbon double bond formed by the removal of two hydrogens.

The term "oxo," as used herein, refers to the radical =O. For example, in certain embodiments, a carbon atom substituted with an oxo group is

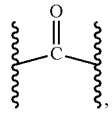

where the symbol ∿∿∿ represents a point of attachment to another group.

The term "thio," used herein, refers to the radical =S. In certain embodiments, a carbon atom substituted with an thio group is

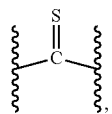

where the ∿∿∿ represents a point of attachment to another group.

The term "imine" as used herein, refers to the radical =NH. In certain embodiments, a carbon atom substituted with an imine group is

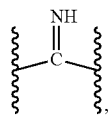

where the symbol ∿∿∿ represents a point of attachment to another group.

The term "substituted imine" as used herein, refers to the radical =N(R), wherein R is a substituent, for example, alkyl. In certain embodiments, a carbon atom substituted with a substituted imine group is

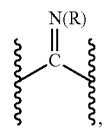

where the symbol ∿∿∿ represents a point of attachment to another group.

The term "amino," as used herein, refers to the radical —$NH_2$.

The term "hydroxyl" or "hydroxy," as used herein, refers to the radical —OH.

The term "carboxyl" as used herein, refers to the radical —$CO_2H$.

The term "thiol," as used herein, refers to the radical —SH. In certain embodiments, thiol refers to the side chain thiol group of a cysteine residue.

The term "substituted thiol," as used herein, refers to a radical such as —SR wherein R is any optionally substituted chemical group described herein. In certain embodiments, "substituted thiol" refers to a radical —SR where R is an alkyl, cycloalkyl, aryl or heteroaryl group as defined herein that may be optionally substituted as defined herein. Representative examples of substituted thiol include, but are not limited to, thiophenyl, thionaphthyl, thiopyridyl, thioisoquinolinyl, as depicted below:

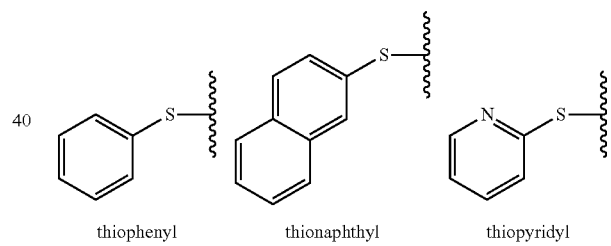

thiophenyl    thionaphthyl    thiopyridyl

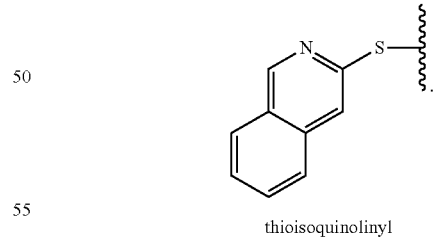

thioisoquinolinyl

The term "sulfonate," as used herein, refers to the radical —$OS(O_2)H$. "Substituted sulfonate" refers to a radical such as —$OS(O_2)R$ wherein R is an alkyl, cycloalkyl, aryl or heteroaryl group as defined herein that may be optionally substituted as defined herein. In certain embodiments, R is selected from lower alkyl, alkyl, aryl and heteroaryl. Representative examples of substituted sulfonate include, but are not limited to, tosylate, mesylate and triflate, as depicted below:

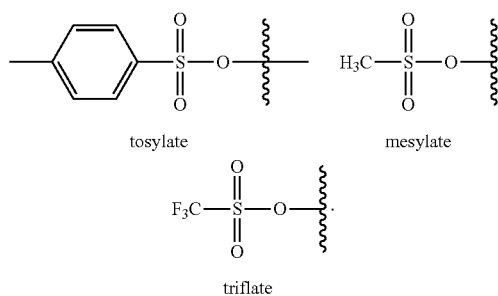

The term "carbocyclic group," "carbocyclic ring," or "carbocycle," as used herein, refers to a hydrocarbon ring or fused ring system containing from 3 to 14 ring atoms, and being fully saturated, or having one or more double bonds between the ring atoms. In certain embodiments, the ring or fused ring system is fully saturated, in which case the carbocycle is a "cycloalkyl group" or "cycloalkyl," as defined herein. In certain embodiments, one or more ring carbon atoms is replaced by a heteroatom, for example, oxygen, sulfur and nitrogen, in which case the carbocycle is a "heterocyclic group," "heterocyclic ring," or "heterocycle." In certain embodiments, the carbocyclic group is an unsaturated aromatic carbocyclic group, which case the carbocycle is an "aryl group" or "aryl," as defined herein. In certain embodiments, the carbocyclic group is an unsaturated aromatic heterocyclic group, which case the carbocycle is an "heteroaryl group" or "heteroaryl," as defined herein.

The term "aryl," as used herein, refers to an unsaturated aromatic carbocyclic group of from 6 to 14 carbon atoms having a single ring (e.g., phenyl) or multiple condensed rings (e.g., naphthyl or anthryl). Preferred aryls include phenyl, biphenyl, naphthyl and the like. Unless otherwise constrained by the definition for the individual substituent, such aryl groups can optionally be substituted with 1 or more substituents, for example, 1 to 5 substituents, such as, hydroxyl, amino, nitro, cyano, chloro, bromo, fluoro, iodo, oxo, carboxyl, $C_{1-6}$ alkoxycarbonyl, $C_{1-6}$ alkyl, $C_{2-6}$ alkenyl, and $C_{1-6}$ alkoxy, and the like. In certain embodiments, such aryl groups can optionally be substituted with 1 to 5 substituents selected from the group consisting of halo, cyano, nitro, $CF_3$—, $CF_3O$—, $CH_3O$—, —$CO_2H$, —$C(O)CH_3$, —$NH_2$, —OH, —SH, —$NHCH_3$, —$N(CH_3)_2$, —SMe and $C_{1-3}$ alkyl.

The term "heteroaryl," as used herein, refers to an aryl ring system having one to four heteroatoms as ring atoms in a heteroaromatic ring system, wherein the remainder of the atoms are carbon atoms. Suitable heteroatoms include oxygen, sulfur and nitrogen. Preferably, the heterocyclic ring system is monocyclic or bicyclic. Unless otherwise constrained by the definition for the individual substituent, such heteroaryl groups can optionally be substituted with 1 or more substituents, for example, 1 to 5 substituents, such as, hydroxyl, amino, nitro, cyano, chloro, bromo, fluoro, iodo, oxo, carboxyl, $C_{1-6}$ alkoxycarbonyl, $C_{1-6}$ alkyl, $C_{2-6}$ alkenyl, and $C_{1-6}$ alkoxy, and the like. In certain embodiments, such heteroaryl groups can optionally be substituted with 1 to 5 substituents selected from the group consisting of halo, cyano, nitro, $CF_3$—, $CF_3O$—, $CH_3O$—, —$CO_2H$, —$C(O)CH_3$, —$NH_2$, —OH, —SH, —$NHCH_3$, —$N(CH_3)_2$, —SMe and $C_{1-3}$ alkyl. Examples of hetroaryl include, but are not limited to:

Where Q if O, $NR^2$ or S

The term "leaving group," as used herein, refers to any group that leaves in the course of a chemical reaction involving the group as described herein and includes but is not limited to halogen, sulfonates (brosylate, mesylate, tosylate triflate etc. . . . ), p-nitrobenzoate and phosphonate groups, for example.

The term "electrophilic leaving group," as used herein, refers to a leaving group that accepts an electron pair to make a covalent bond. In general, electrophiles are susceptible to attack by complementary nucleophiles, including the reduced thiols from the disulfide bond of an antibody.

The term "electrophilic leaving group that reacts selectively with thiols," as used herein, refers to electrophilic leaving group that reacts selectively with thiols, over other nucleophiles. In certain embodiments, an electrophilic leaving group that reacts selectively with thiols reacts selectively with the reduced thiols from the disulfide bond of an antibody.

The terms "cell proliferative disorder" and "proliferative disorder" refer to disorders that are associated with some degree of abnormal cell proliferation. In one aspect, the cell-proliferative disorder is cancer.

"Tumor," refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive. The terms "cancer" and "cancerous" refer to the physiological condition in mammals that is typically characterized by unregulated cell growth. Examples of cancer include, but are not limited to, carcinoma, lymphoma, blastoma, sarcoma and leukemia or lymphoid malignancies.

A "therapeutically effective amount" means that amount of a modified antibody, composition, or formulation disclosed herein which, when administered to a human suffering from a cancer, is sufficient to effect treatment for the cancer. "Treating" or "treatment" of the cancer includes one or more of:

(1) limiting/inhibiting growth of the cancer, e.g., limiting its development;
(2) reducing/preventing spread of the cancer, e.g., reducing/preventing metastases;
(3) relieving the cancer, e.g., causing regression of the cancer;
(4) reducing/preventing recurrence of the cancer; and
(5) palliating symptoms of the cancer.

Cancers of interest for treatment include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, oral cancer, liver cancer, bladder cancer, cancer of the urinary tract, hepatoma, breast cancer including, for example, HER2-positive breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, acute myeloid leukemia (AML), chronic lymphocytic leukemia (CML), multiple myeloma and B-cell lymphoma, brain cancer, head and neck cancers and associated metastases.

Abbreviations/Acronyms

DPBS: Dulbecco's phosphate-buffered saline; DTPA: diethylenetriaminepentaacetic acid; DTT: dithiothreitol; PBS: phosphate-buffered saline; PEG: poly(ethyleneglycol); and TCEP: tris(2-carboxyethyl)phosphine.

Abbreviations/Acronyms (Antibodies)

ATZ: alemtuzumab; ATM: anitumumab; BCZ: bevacizumab; BTX: brentuximab; CTX: cetuximab; GTZ: gemtuzumab; GBT: glembatumumab; ITZ: inotuzumab; ILM: ipilimumab; LVT: lovortumumab; MTZ: milatuzumab; OTM: ofatumumab; RTX: rituximab; TTM: tositumomab; and TTZ: trastuzumab.

Compounds

The compounds used to make the modified antibodies disclosed herein may be prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions, vols.* 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations, VCH Publishers, New York*, 1989. In some instances, the compounds used to make the modified antibodies disclosed herein may be purchased from commercial sources.

The following illustrate various embodiments of the compounds disclosed herein, which may be synthesized by these methods:

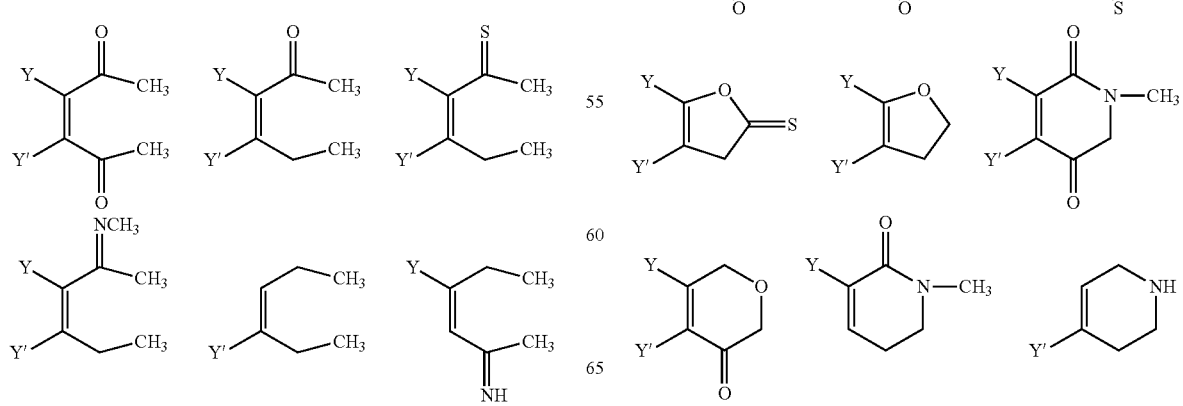

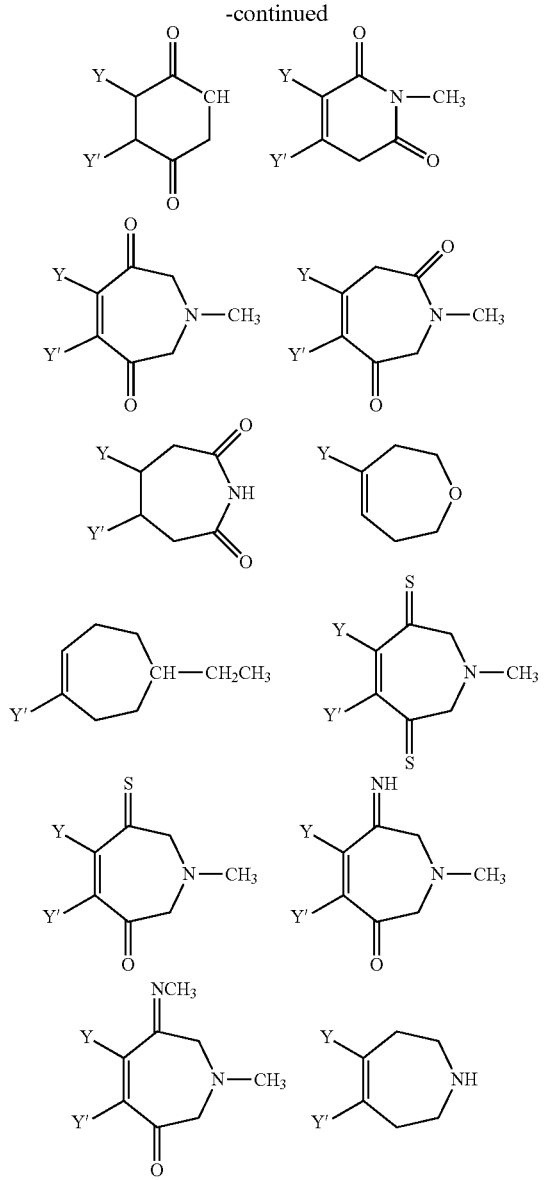

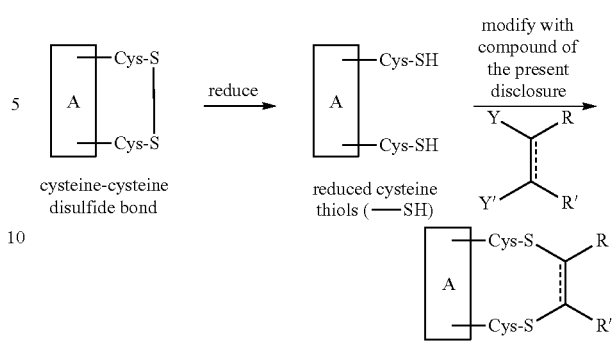

The above embodiments are merely illustrative, and not meant to be limiting.

Modified Antibodies

Figure 8:
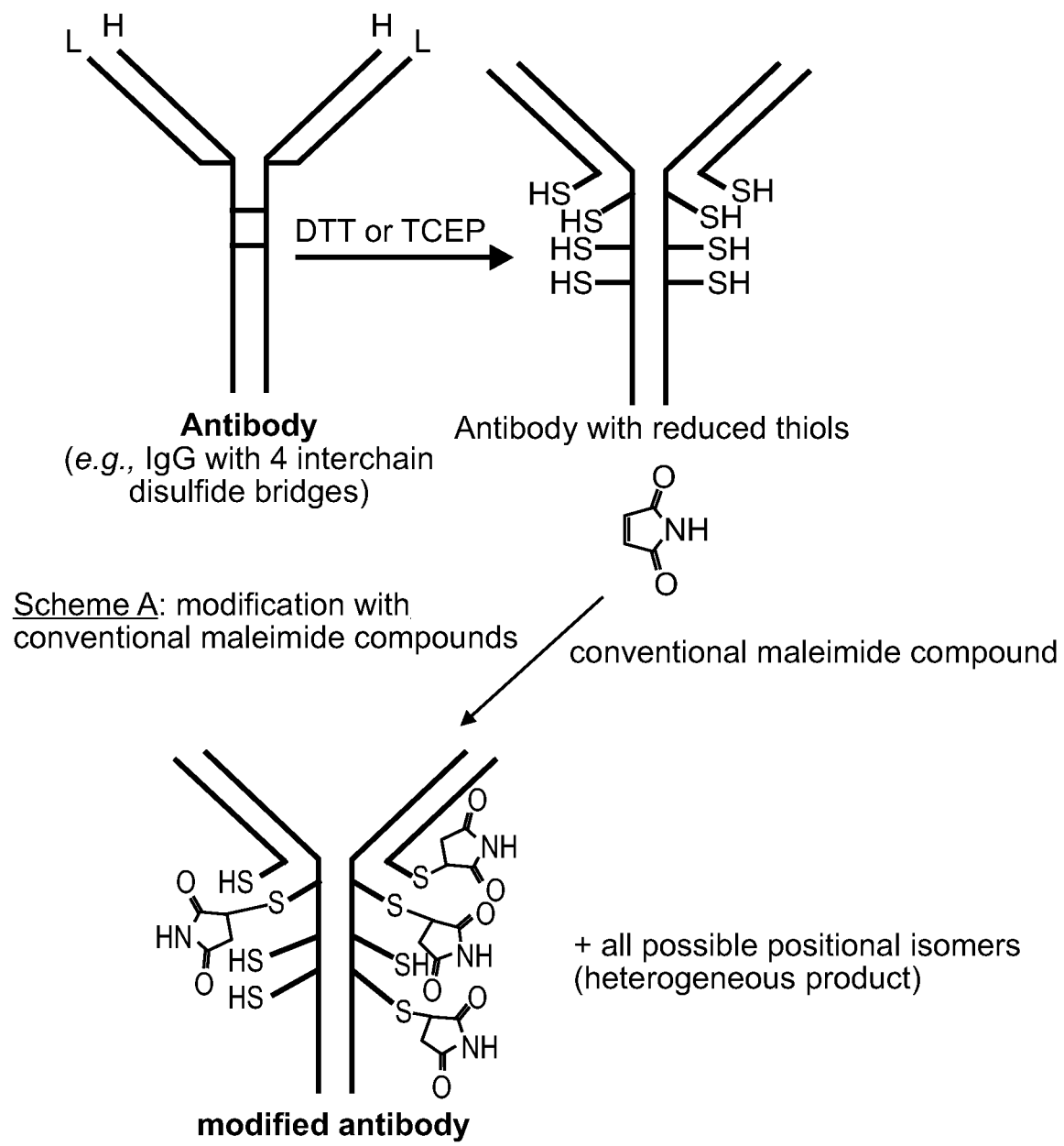
FIG. 8: Scheme A illustrating that reduction and opening of the cysteine-cysteine disulfide bonds to give free thiols for conjugation decreases the stability of the antibody, and the formation of the modified antibody by reaction of the reduced thiols does not re-form the interchain disulfide bond

Compounds that coordinate to cysteine thiols of the antibody have employed monofunctional compounds, of which maleimide is an example. Reduction and opening of the cysteine-cysteine disulfide bonds to give free thiols for conjugation decreases the stability of the antibody, and the formation of the modified antibody by reaction of the reduced thiols does not re-form the interchain disulfide bond, as illustrated in FIG. 8.

As a result, a heterogenous mixture of modified is produced, which may comprise all possible positional isomers of conjugated compound to cysteine thiol, and may comprise all possible compound antibody ratios (1, 2, 3, 4, and 8).

Figure 9:
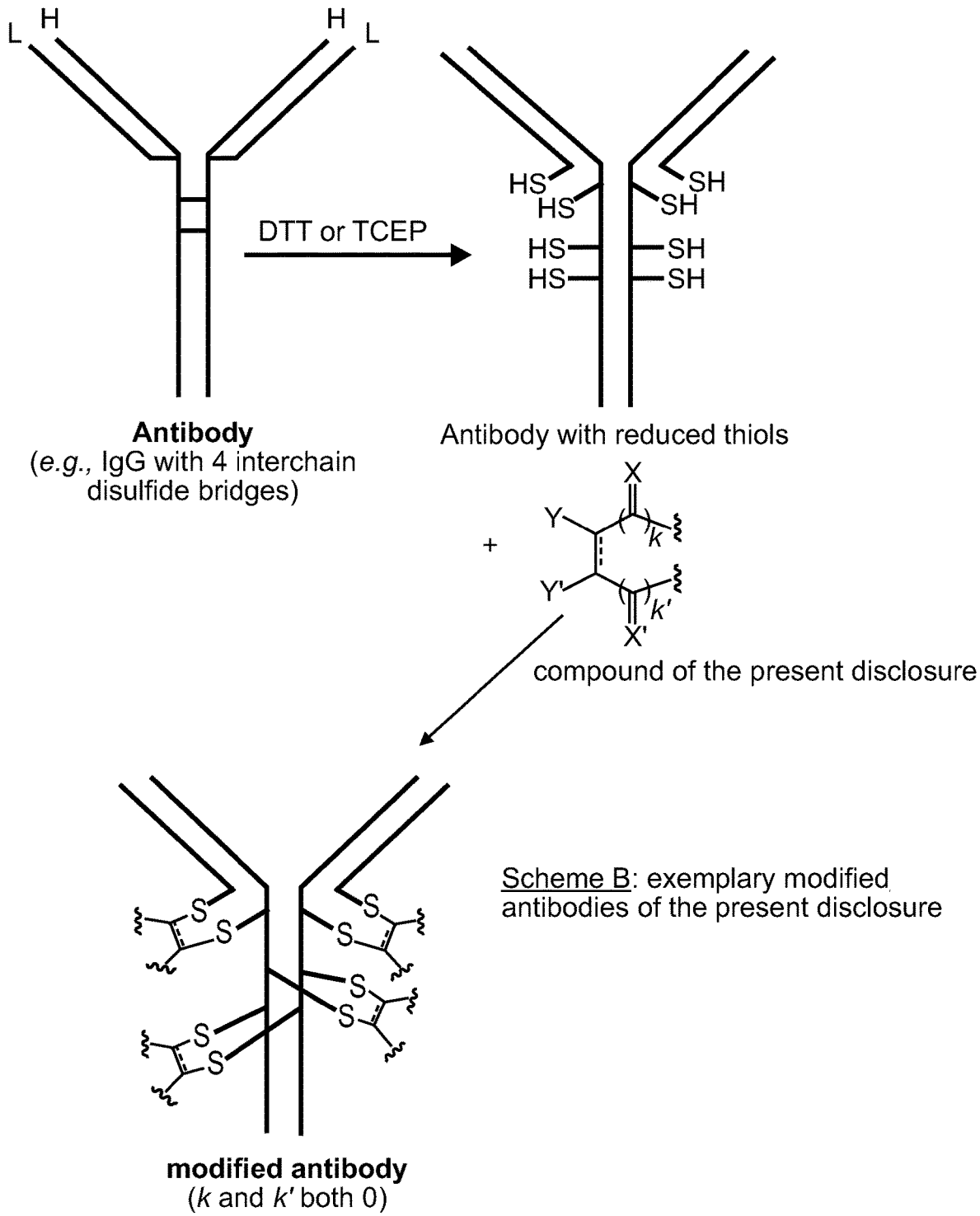
FIG. 9: Scheme B illustrating that reaction of a compound disclosed herein with the two cysteine thiols gives a modified antibody conjugate with one compound per disulfide (e.g., one or more interchain disulfides) connected through two thioesther bonds

In contrast, the compounds disclosed herein contain two reactive functional groups (e.g., Y and Y' in the scheme below) that selectively target the two sulfur atoms of the thiols of a reduced cysteine-cysteine disulfide bond (e.g., interchain disulfide bond), as illustrated below:

Reaction of the compound with the two cysteine thiols gives a modified antibody conjugate with one compound per disulfide (e.g., one or more interchain disulfides) connected through two thioether bonds, as depicted in FIG. 4 and FIG. 9.

Homogeneous modified antibodies are produced, for example, with a compound to antibody ratio of 4. Scheme B depicts a homogenous modified antibody, where, for example, the four (4) interchain disulfide bonds of the antibody (e.g., 2 H—H disulfide bonds, and 2 H-L disulfide bonds) are conjugated.

Unlike conventional methods for cysteine conjugation, the reaction reforms a covalently bonded structure between the 2 cysteine sulfur atoms and therefore does not compromise and/or may enhance the overall stability of the antibody. The overall result is replacement of a relatively labile disulfide bond (e.g., interchain disulfide bond) with a stable "staple" or "snap" between the cysteines. The monosubstituted compounds (where one of Y and Y' is hydrogen) are also effectively bifunctional in conjugation with the antibody because the double bond is capable of conjugation to one of the cysteine sulfur atoms and the Y group with the other.

Preparation of the Disclosed Compounds

The compounds disclosed herein may be prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

Preparation of Modified Antibodies

Antibodies, typically monoclonal antibodies, are selected for binding to a specific antigen (e.g., cancer target), and purified and characterized. Therapeutic modified antibodies are prepared by standard methods for cysteine conjugation, such as by methods analogous to those of Hamblett et al., "Effects of Drug Loading on the Antitumor Activity of a Monoclonal Antibody Drug Conjugate", *Clin. Cancer Res.* 2004, 10, 7063-7070; Doronina et al., "Development of potent and highly efficacious monoclonal antibody auristatin conjugates for cancer therapy", *Nat. BiotechnoL*, 2003, 21(7), 778-784; and Francisco et al., "cAC10-vcMMAE, an anti-CD30-monomethylauristatin E conjugate with potent and selective antitumor activity", *Blood*, 2003, 102, 1458-1465. Modified antibody with four compounds per antibody are prepared by partial reduction of the antibody with an excess of a reducing reagent such as DTT or TCEP at 37° C.

for 30 min, then the buffer exchanged by elution through SEPHADEX® G-25 resin with 1 mM DTPA in DPBS. The eluent is diluted with further DPBS, and the thiol concentration of the antibody may be measured using 5,5'-dithiobis (2-nitrobenzoic acid) [Ellman's reagent]. An excess, for example 5-fold, of the chemical compound is added at 4° C. for 1 hr, and the conjugation reaction may be quenched by addition of a substantial excess, for example 20-fold, of cysteine. The resulting modified antibody mixture may be purified on SEPHADEX G-25 equilibrated in PBS to remove unreacted compound, desalted if desired, and purified by size-exclusion chromatography. The resulting modified antibody may then be then sterile filtered, for example, through a 0.2 pM filter, and lyophilized if desired for storage.

The formation of a modified antibody is described herein, illustrated by Scheme B above depicts a "Y"-shaped structure denoting an antibody, for example, an IgG1, where all four (4) interchain disulfide bonds of the antibody (2 H—H disulfide bonds, and 2 H-L disulfide bonds) are modified by conjugation with compound with a ratio of 4.

The Method:

In one aspect, provided herein is a method of modifying an antibody by reacting the antibody with a compound comprising a moiety of the following formula (I):

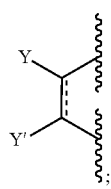

(I)

or an enantiomer, diasteriomer, or mixtures thereof;
wherein:
each Y and Y' is independently hydrogen or an electrophilic leaving group that reacts selectively with thiols, provided if one of Y and Y' is hydrogen, the other is the electrophilic leaving group;
the ===== bond represents a single or a double bond; and
the symbol ᗡᗡᗡ represents a point of attachment to another group.

In certain embodiments of the method, the antibody is modified by reacting the thiols of two cysteine residues from at least one reduced interchain cysteine-cysteine disulfide with the compound.

In certain embodiments of the method, the ===== bond represents a single bond. In certain embodiments of the method, the ===== bond represents a double bond.

In certain embodiments of the method, the groups to which the moiety is attached do not include a polyether, for example, a PEG. In certain embodiments, the groups to which the moiety is attached do not include a cytotoxin. In certain embodiments, the groups to which the moiety is attached do not include a linker, for example, a PEGylated linker. In certain embodiments, the groups to which the moiety is attached do not include a linker conjugated to a cytotoxin.

In certain embodiments of the method, the compound has the following formula (Ia):

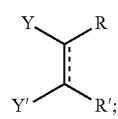

(Ia)

or an enantiomer, diasteriomer, or mixtures thereof;
wherein:
each R and R' is independently hydrogen or $C_{1-6}$ alkyl, wherein one or more carbons in the $C_{1-6}$ alkyl are optionally substituted by a group selected from an oxo, a thio, an imine, and a substituted imine; or
R and R', together with the two carbons from the single or double bond to which they are attached, form a saturated or unsaturated carbocyclic ring containing from four to seven ring atoms; wherein, excluding the two carbons from the single or double bond, one or more of the ring carbon atoms are optionally replaced by a heteroatom selected from 0 and N; wherein, excluding the two carbons from the single or double bond, one or more of the ring carbon atoms are optionally substituted by a group selected from an oxo, a thio, an imine, a substituted imine, and a $C_{1-3}$ alkyl; and wherein, if present, the ring nitrogen atom is optionally substituted by a $C_{1-3}$ alkyl.

In certain embodiments of the method, the moiety has one of the following formulas (Ib) and (Ic):

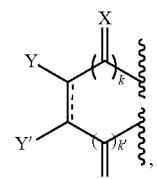

(Ib)

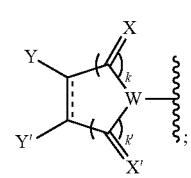

(Ic)

or an enantiomer, diasteriomer, or mixtures thereof;
wherein:
each X and X' is independently absent, O, S, NH, or $NR^1$ wherein $R^1$ is $C_{1-3}$ alkyl;
W is —O—, =N—, or =CH—; and
each k and k' is independently an integer of 0, 1, or 2.

In certain embodiments of the method, the compound has one of the following formulas (Id) and (Ie):

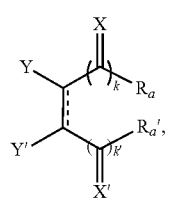

(Id)

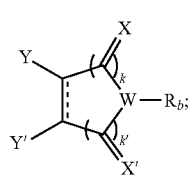
(Ie)

wherein,

Each $R_a$, $R_{a'}$ and $R_b$ is independently hydrogen, $C_{1-3}$ alkyl, or absent.

In certain embodiments of the method, where the moiety is of formula (Ib), k and k' are both 0 (X and X' are both absent), as depicted below:

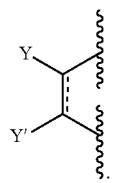

In certain embodiments of the method, where the moiety is of formula (Ib), k is 0 (X is absent), and k' is 1, as depicted below:

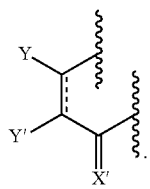

In certain embodiments of the method, where the moiety is of formula (Ib), k is 1, and k' is 0 (X' is absent), as depicted below:

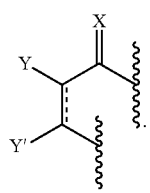

In certain embodiments of the method, where the moiety is of formula (Ib), k and k' are both 1, and each X and X' is independently O or S; as depicted below:

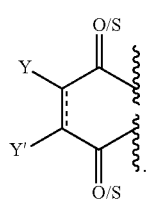

In certain embodiments of the method, where the moiety is of formula (Ib), k and k' are both 1, and X and X' are both absent, as depicted below:

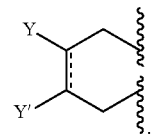

In certain embodiments of the method, where the moiety is of formula (Ib), k and k' are both 1, X is O or S, and X' is absent, as depicted below:

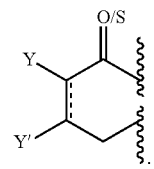

In certain embodiments of the method, where the moiety is of formula (Ib), k and k' are both 1, X is absent, and X' is O or S, as depicted below:

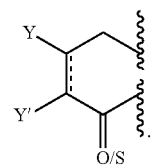

Similarly, one of ordinary skill in the art will be able to envision all possible embodiments of k, k', X and X' with regard to the moiety of formula (Ib).

In certain embodiments of the method, where the moiety is of formula (Ic), k is 0 (X is absent) and k' is 2, as depicted below:

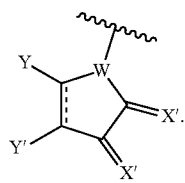

In certain subembodiments of the above embodiment, one or both of X' may also absent, as depicted below:

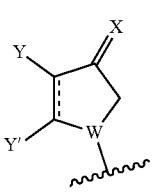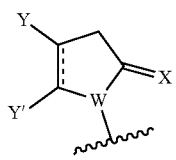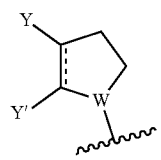

In certain embodiments of the method, where the moiety is of formula (Ic), k is 2 and k' is 0 (X' is absent), as depicted below:

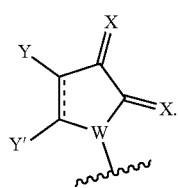

In certain subembodiments of the above embodiment, one or both of X are also absent, as depicted below:

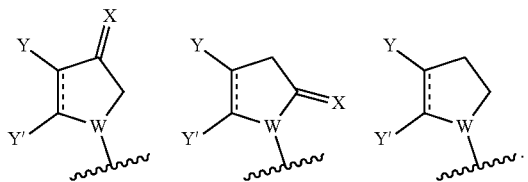

In certain embodiments of the method, where the moiety is of formula (Ic), k and k' are both 1, and each X and X' is independently O or S; as depicted below:

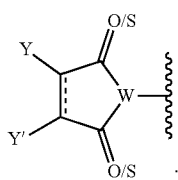

In certain embodiments of the method, where the moiety is of formula (Ic), k and k' are both 1, and X and X' are both absent, as depicted below:

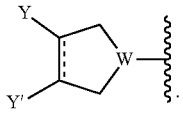

In certain embodiments of the method, where the moiety is of formula (Ic), k is 1, k' is 2, and X and X' are both absent, as depicted below:

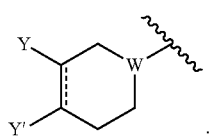

In certain embodiments of the method, where the moiety is of formula (Ic), k is 2, k' is 1, and X and X' are both absent, as depicted below:

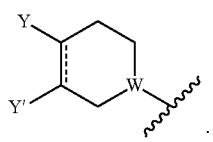

In certain embodiments of the method, where the moiety is of formula (Ic), k is 2, k' is 2, and X and X' are both absent, as depicted below:

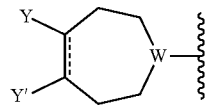

In certain embodiments of the method, where the moiety is of formula (Ic), k and k' are both 1, X is O or S, and X' is absent, as depicted below:

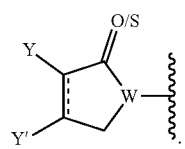

In certain embodiments of the method, where the moiety is of formula (Ic), k and k' are both 1, X is absent, and X' is O or S, as depicted below:

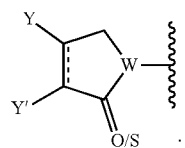

In certain embodiments of the method, where the moiety is of formula (Ic), k is 1, k' is 2, X is O or S, and X' is absent, as depicted below:

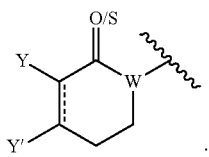

In certain embodiments of the method, where the moiety is of formula (Ic), k is 2, k' is 1, X is absent, and X' is O or S, as depicted below:

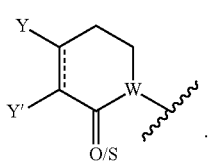

Similarly, one of ordinary skill in the art will be able to envision all possible embodiments of k, k', X and X' with regard to the moiety of formula (Ic).

In certain embodiments of the method, each Y and Y' is independently hydrogen or an electrophilic leaving group that reacts selectively with thiol.

In certain embodiments of the method, each Y and Y' is independently selected from the group consisting of a halo, a substituted thiol, and a substituted sulfonate. In certain embodiments, each Y and Y' is independently selected from the group consisting of chloro, bromo, fluoro, and iodo. In certain embodiments, each Y and Y' is independently selected from an optionally substituted thiophenyl, an optionally substituted thionaphthyl, an optionally substituted thiopyridyl, an optionally substituted isoquinoline, and an optionally substituted phenylsulfonate.

In certain embodiments of the method, each Y and Y' is independently selected from the group consisting of:

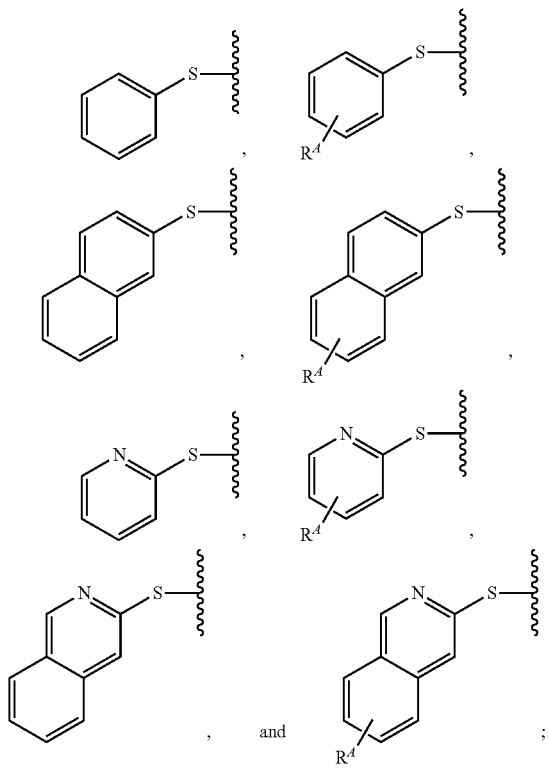

wherein
$R_4$ is selected from the group consisting of hydroxyl, amino, nitro, cyano, chloro, bromo, fluoro, iodo, oxo, carboxyl, $C_{1-6}$ alkoxycarbonyl, $C_{1-6}$ alkyl, $C_{2-6}$ alkenyl, and $C_{1-6}$ alkoxy.

In certain embodiments of the method, each Y and Y' is independently selected from the group consisting of:

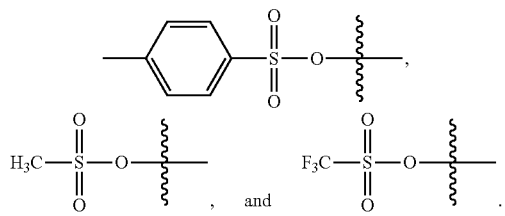

The Antibody (A):

In certain embodiments, disclosed herein are antibodies and antibody fragments (see, e.g., FIG. 2) for use in the methods disclosed herein.

In certain embodiments, A is an antibody or an antibody fragment. In certain embodiments, A is a monoclonal antibody or monoclonal antibody fragment.

In certain embodiments, the antibody (A) is a monoclonal antibody or a humanized antibody. In certain embodiments, the antibody is specific to a cancer antigen. In another embodiment, the antibody employed in the modified antibodies disclosed herein is selected from the group consisting of alemtuzumab, bevacizumab, cetuximab, ipilimumab, ofatumumab, anitumumab, rituximab, tositumomab, inotuzumab, glembatumumab, lovortuzumab, milatuzumab and trastuzumab.

The Modified Antibody:

In another aspect, provided herein is a modified antibody of the following formula (ll):

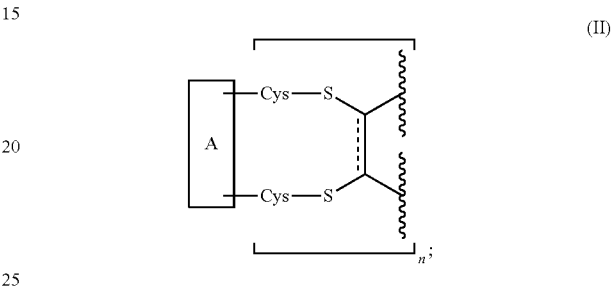

(II)

wherein:
A is an antibody or antibody fragment;
the two depicted cysteine residues are from at least one reduced interchain cysteinecysteine disulfide bond in A;
n is an integer from 1 to 13;
the ====== bond represents a single or a double bond; and
the symbol ∿∿∿ represents a point of attachment to another group.

In certain embodiments of the modified antibody, the ====== bond represents a single bond. In certain embodiments of the modified antibody, the bond ====== represents a double bond.

In certain embodiments, the modified antibody does not include an ADC. In certain embodiments, the modified antibody does not include an antibody with a linker (e.g., PEGylated linker). In certain embodiments, the modified antibody does not include an antibody conjugated to a cytotoxin (e.g., a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, an anti-metabolite, Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, or Vincristine). In certain embodiments, the modified antibody does not include an antibody conjugated through a linker to a cytotoxin.

In certain embodiments of the modified antibody, the groups to which the moiety is attached do not include a polyether, for example, a PEG. In certain embodiments, the groups to which the moiety is attached do not include a cytotoxin. In certain embodiments, the groups to which the moiety is attached do not include a linker, for example, a PEGylated linker. In certain embodiments, the groups to which the moiety is attached do not include a polyether (e.g., PEG) linker conjugated to a cytotoxin.

In certain embodiments, the modified antibody has the following formula (IIa):

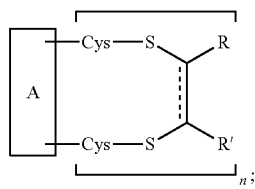

(IIa)

wherein:
each R and R' is independently hydrogen or $C_{1-6}$ alkyl, wherein one or more carbons in the $C_{1-6}$ alkyl are optionally substituted by a group selected from an oxo, a thio, an imine, and a substituted imine; or
R and R', together with the two carbons from the single or double bond to which they are attached, form a saturated or unsaturated carbocyclic ring containing from four to seven ring atoms; wherein, excluding the two carbons from the single or double bond, one or more of the ring carbon atoms are optionally replaced by a heteroatom selected from O and N; wherein, excluding the two carbons from the single or double bond, one or more of the ring carbon atoms are optionally substituted by a group selected from an oxo, a thio, an imine, a substituted imine, and a $C_{1-3}$ alkyl; and wherein, if present, the ring nitrogen atom is optionally substituted by a $C_{1-3}$ alkyl.

In certain embodiments, the modified antibody has one of the following formulas (IIb) and (IIc):

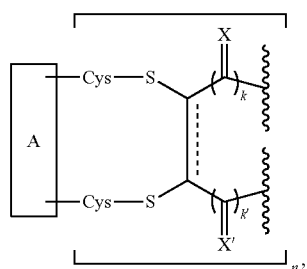

(IIb)

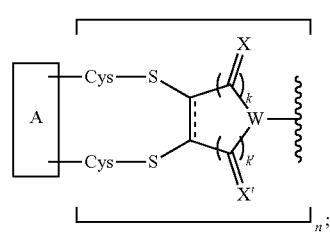

(IIc)

wherein:
each X and X' is independently absent, O, S, NH, or $NR^1$ wherein $R^1$ is $C_{1-3}$ alkyl;
W is —O—, =N—, or =CH—; and
each k and k' is independently an integer of 0, 1, or 2.

In certain embodiments, the modified antibody has one of the following formulas (IId) and (IIe):

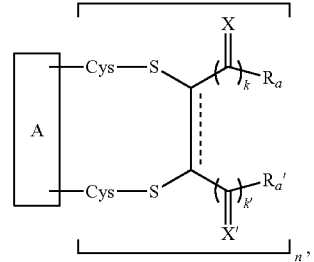

(IId)

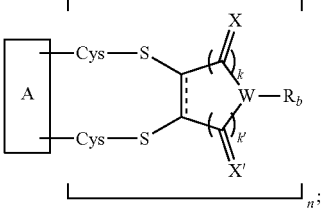

(IIe)

wherein:
each $R_a$, $R_a'$ and $R_b$ is independently hydrogen, $C_{1-3}$ alkyl, or absent.

In certain embodiments of the modified antibody, A is an antibody that is specific to a cancer antigen. In certain embodiments, A is selected from the group consisting of alemtuzumab, anitumumab, bevacizumab, brentuximab, cetuximab, gemtuzumab, glembatumumab, inotuzumab, ipilimumab, lovortumumab, milatuzumab, ofatumumab, rituximab, tositumomab, and trastuzumab.

In certain embodiments of the modified antibody, where the antibody is of formula (IIb), k and k' are both 0 (X and X' are both absent), as depicted below:

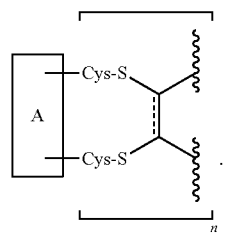

In certain embodiments of the modified antibody, where the antibody is of formula (IIb), k is 0 (X is absent), and k' is 1, as depicted below:

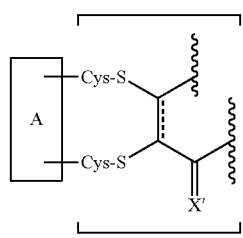

In certain embodiments of the modified antibody, where the antibody is of formula (IIb), k is 1, and k' is 0 (X' is absent), as depicted below:

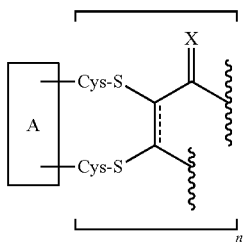

In certain embodiments of the modified antibody, where the antibody is of formula (IIb), k and k' are both 1, and each X and X' is independently O or S; as depicted below:

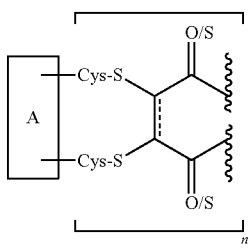

In certain embodiments of the modified antibody, where the antibody is of formula (IIb), k and k' are both 1, and X and X' are both absent, as depicted below:

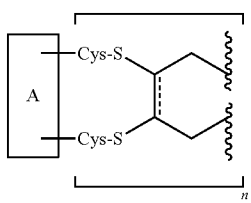

In certain embodiments of the modified antibody, where the antibody is of formula (IIb), k and k' are both 1, X is O or S, and X' is absent, as depicted below:

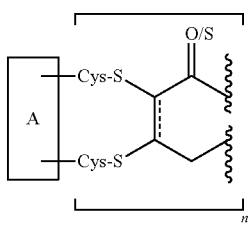

In certain embodiments of the modified antibody, where the antibody is of formula (IIb), k and k' are both 1, X is absent, and X' is O or S, as depicted below:

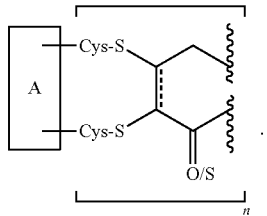

Similarly, one of ordinary skill in the art will be able to envision all possible embodiments of k, k', X and X' with regard to the antibody of formula (IIb).

In certain embodiments of the modified antibody, where the antibody is of formula (IIc), k is 0 (X is absent) and k' is 2, as depicted below:

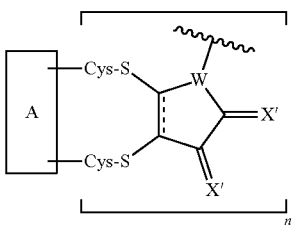

In certain subembodiments of the above embodiment, one or both of X' may also absent, as depicted below:

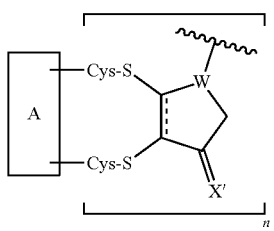

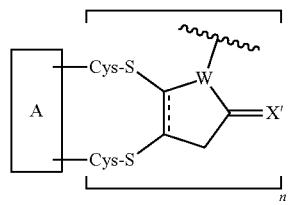

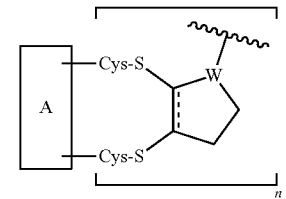

In certain embodiments of the modified antibody, where the antibody is of formula (IIc), k is 2 and k' is 0 (X' is absent), as depicted below:

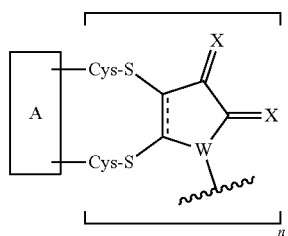

In certain subembodiments of the above embodiment, one or both of X are also absent, as depicted below:

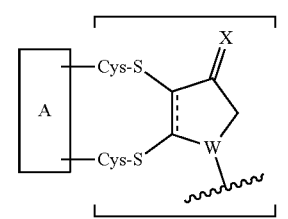

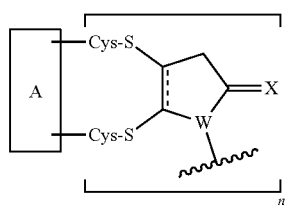

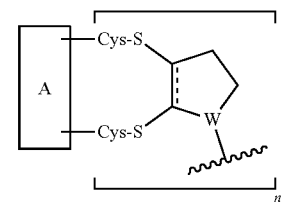

In certain embodiments of the modified antibody, where the antibody is of formula (IIc), k and k' are both 1, and each X and X' is independently O or S; as depicted below:

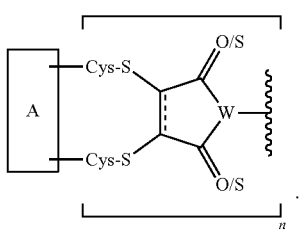

In certain embodiments of the modified antibody, where the antibody is of formula (IIc), k and k' are both 1, and X and X' are both absent, as depicted below:

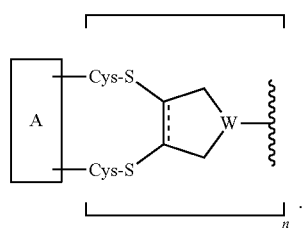

In certain embodiments of the modified antibody, where the antibody is of formula (IIc), k is 1, k' is 2, and X and X' are both absent, as depicted below:

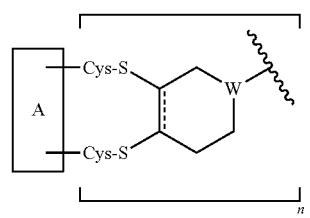

In certain embodiments of the modified antibody, where the antibody is of formula (IIc), k is 2, k' is 1, and X and X' are both absent, as depicted below:

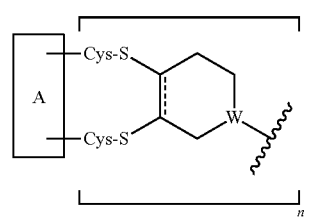

In certain embodiments of the modified antibody, where the antibody is of formula (IIc), k is 2, k' is 2, and X and X' are both absent, as depicted below:

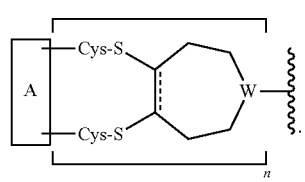

In certain embodiments of the modified antibody, where the antibody is of formula (IIc), k and k' are both 1, X is O or S, and X' is absent, as depicted below:

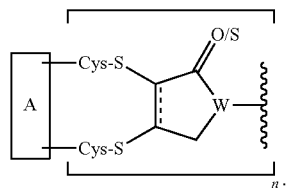

In certain embodiments of the modified antibody, where the antibody is of formula (IIc), k and k' are both 1, X is absent, and X' is O or S, as depicted below:

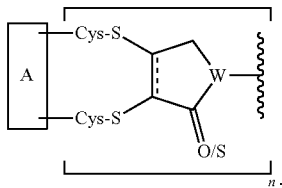

In certain embodiments of the modified antibody, where the antibody is of formula (IIc), k is 1, k' is 2, X is O or S, and X' is absent, as depicted below:

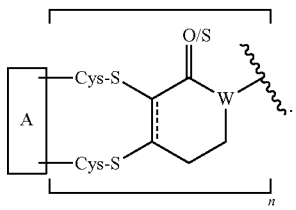

In certain embodiments of the modified antibody, where the antibody is of formula (IIc), k is 2, k' is 1, X is absent, and X' is O or S, as depicted below:

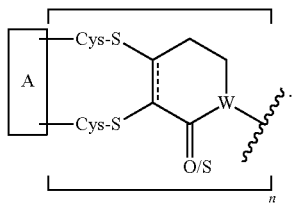

Similarly, one of ordinary skill in the art will be able to envision all possible embodiments of k, k', X and X' with regard to the antibody of formula (IIc).

Assays

The antibodies disclosed herein may be assayed for binding affinity to and specificity for the desired antigen by any of the methods conventionally used for the assay of antibodies; and they may be assayed for efficacy as therapeutics. A person of ordinary skill in the art will have no difficulty, considering that skill and the literature available, in determining suitable assay techniques; from the results of those assays, in determining suitable doses to test in humans as therapeutic agents, and, from the results of those tests, in determining suitable doses to use to treat diseases, disorders or conditions in humans.

Formulation and Administration

The antibodies disclosed herein will typically be formulated as solutions for intravenous administration, or as lyophilized concentrates for reconstitution to prepare intravenous solutions (to be reconstituted, e.g., with normal saline, 5% dextrose, or similar isotonic solutions). They will typically be administered by intravenous injection or infusion. A person of ordinary skill in the art of pharmaceutical formulation, especially the formulation of therapeutic antibodies, will have no difficulty, considering that skill and the literature available, in developing suitable formulations.

EXAMPLES

Synthesis of Compounds

The following procedures may be employed for the preparation of the compounds disclosed herein. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

In some cases, protective groups may be introduced and finally removed. Suitable protective groups for amino, hydroxy and carboxy groups are described in Greene et al., Protective Groups in Organic Synthesis, Second Edition, John Wiley and Sons, New York, 1991. Standard organic chemical reactions can be achieved by using a number of different reagents, for examples, as described in Larock: Comprehensive Organic Transformations, VCH Publishers, New York, 1989.

Example 1: Antibody Modified with 1,2-dibromoethene

Figure 10:
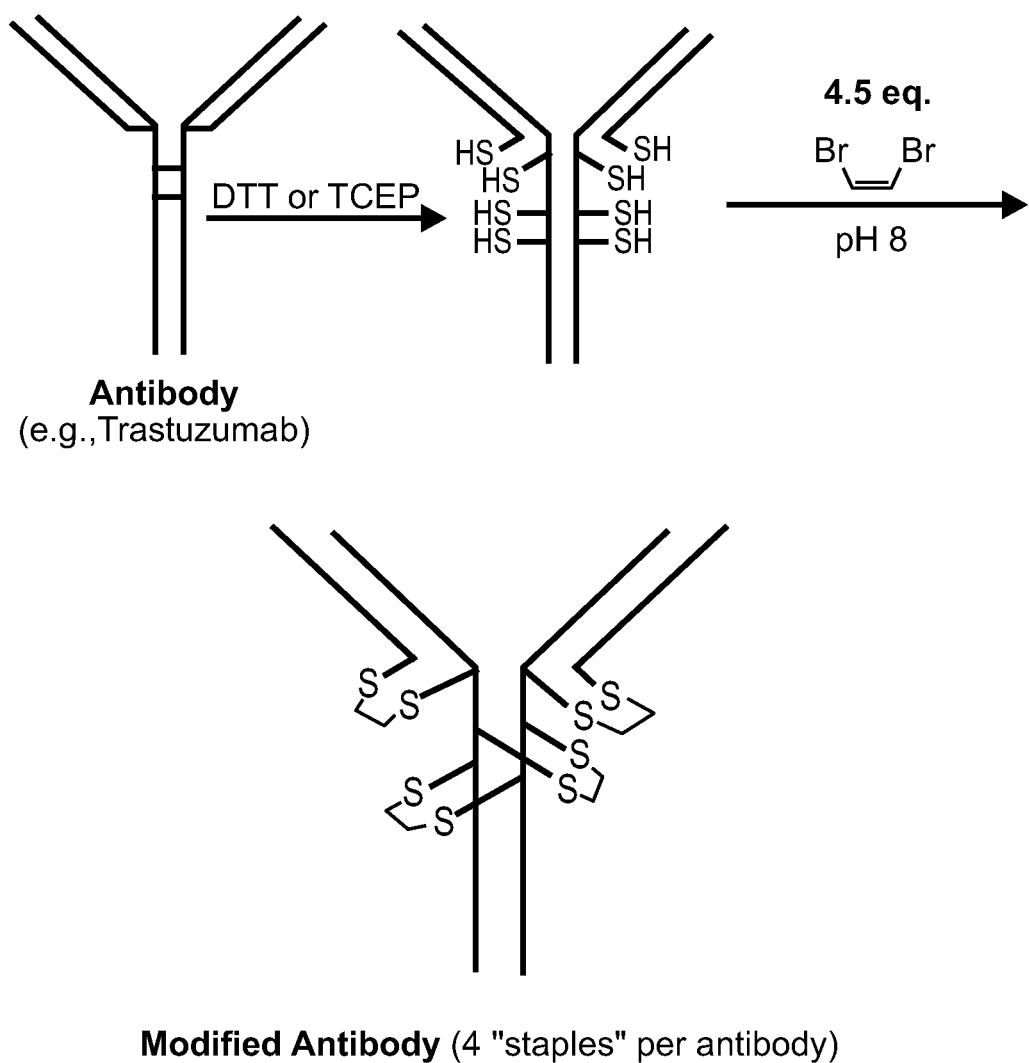
FIG. 10: Modification of an Antibody with 1,2-dibromoethene as described in Example 1

Trastuzumab, 1 mL of a 20 mg/mL solution in pH 7.4 PBS (Gibco Mg and Ca free) with 1 mM DTPA, is loaded into a sterile 1.7 mL Eppendorf tube, then 2.75 equivalents of TCEP hydrochloride (Sigma ampule 0.5M concentration), is added and the mixture incubated at 37° C. for 1 hour to give an average of 4 free thiol pairs per trastuzumab (this can be verified by Ellman's colorimetric assay—see Ellman, "Tissue sulfhydryl groups", Arch. Biochem. Biophys, 1959, 82, 70-77 or later papers referring to this assay). The reduced antibody solution is cooled in an icebath at about 0° C. for 15 minutes; then a solution of about 4.5 equivalents of 1,2-dibromoethene in dimethylsulfoxide is added and the mixture incubated at 37° C. for 2 hours (or at 4° C. for 20 hours). The resulting modified antibody is purified by size-exclusion chromatography (GE AKTA pure chromatographic system) or PD10 desalting column. A depiction of the described modification is shown in FIG. 10.

Example 2: Antibody Modified with 1,2-dibromopentan-3-one

Figure 11:
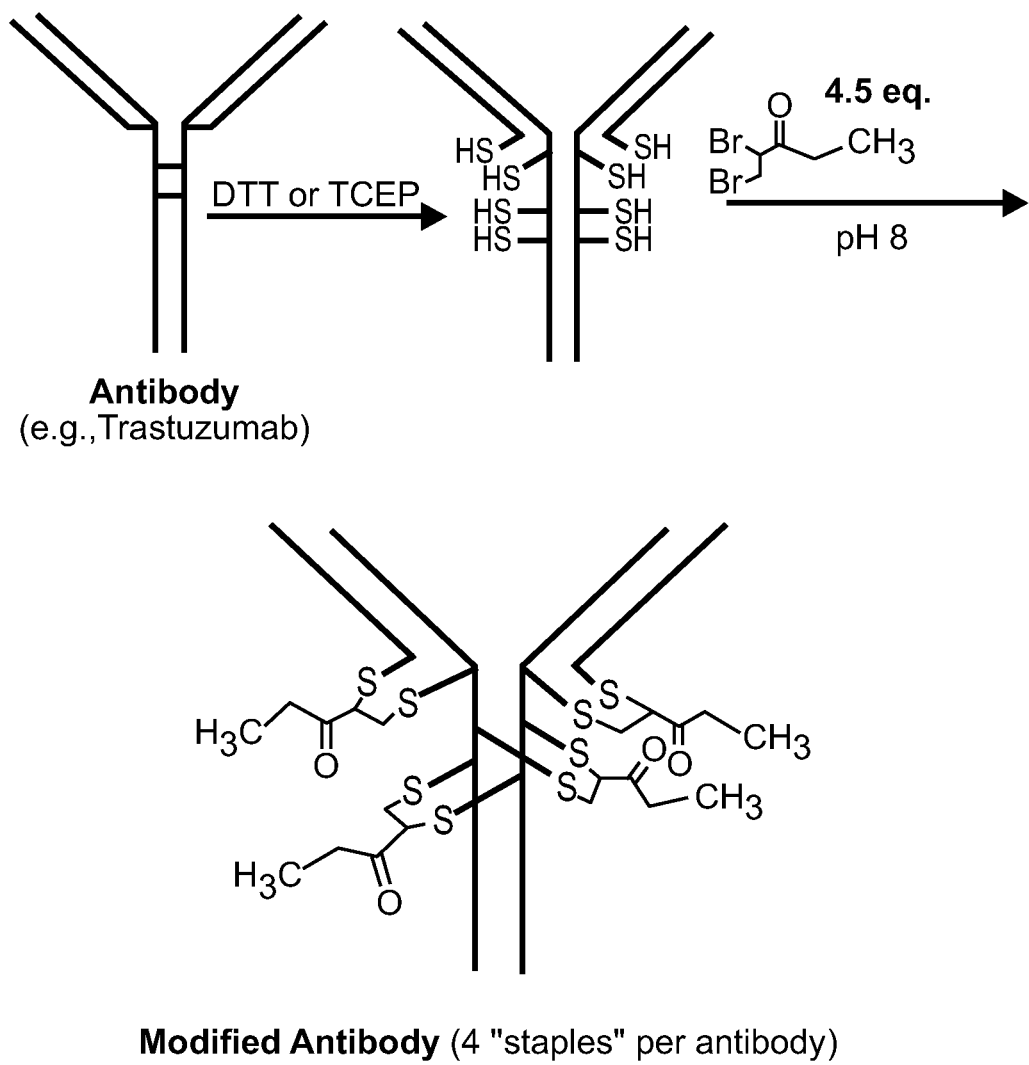
FIG. 11: Modification of an Antibody with 1,2-dibromopentan-3-one as described in Example 2

Trastuzumab, 1 mL of a 20 mg/mL solution in pH 7.4 PBS (Gibco Mg and Ca free) with 1 mM DTPA, is loaded into a sterile 1.7 mL Eppendorf tube, then 2.75 equivalents of TCEP hydrochloride (Sigma ampule 0.5M concentration), is added and the mixture incubated at 37° C. for 1 hour to give an average of 4 free thiol pairs per trastuzumab (this can be verified by Ellman's colorimetric assay—see Ellman, "Tissue sulfhydryl groups", Arch. Biochem. Biophys, 1959, 82, 70-77 or later papers referring to this assay). The reduced antibody solution is cooled in an ice-bath at about 0° C. for 15 minutes; then a solution of about 4.5 equivalents of 1,2-dibromopentan-3-one in dimethylsulfoxide is added and the mixture incubated at 37° C. for 2 hours (or at 4° C. for 20 hours). The resulting modified antibody is purified by size-exclusion chromatography (GE AKTA pure chromatographic system) or PD10 desalting column. A depiction of the described modification is shown in FIG. 11.

Figure 12:
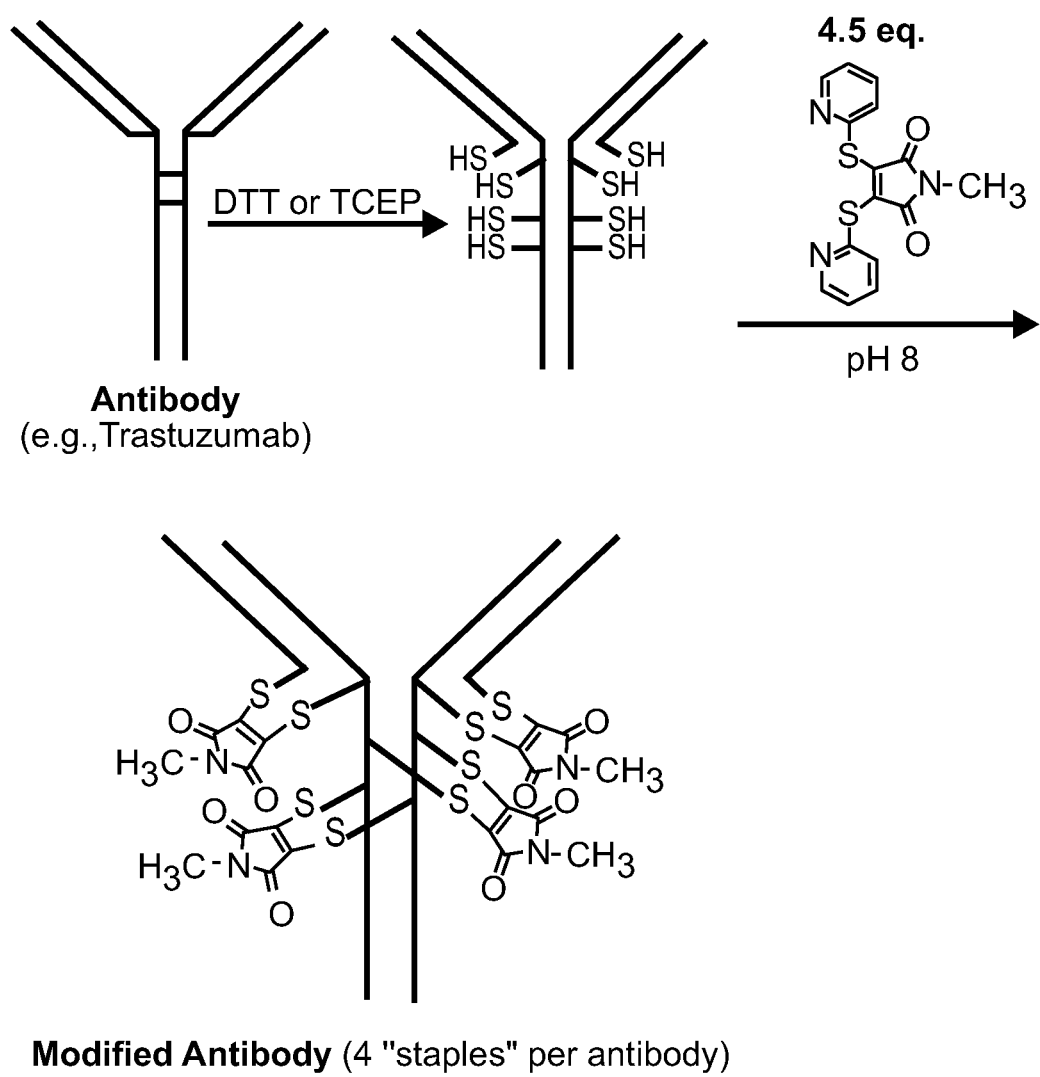
FIG. 12: Modification of an Antibody with 1-methyl-3,4-bis(pyridin-2-ylthio)-1H-pyrrole-2,5-dione as described in Example 3

Example 3: Modified Antibody with 1-methyl-3,4-bis(pyridin-2-ylthio)-1H-pyrrole-2,5-dione Trastuzumab, 1 mL of a 20 mg/mL solution in pH 7.4 PBS (Gibco Mg and Ca free) with 1 mM DTPA, is loaded into a sterile 1.7 mL Eppendorf tube, then 2.75 equivalents of TCEP hydrochloride (Sigma ampule 0.5M concentration), is added and the mixture incubated at 37° C. for 1 hour to give an average of 4 free thiol pairs per trastuzumab (this can be verified by Ellman's colorimetric assay—see Ellman, "Tissue sulfhydryl groups", *Arch. Biochem. Biophys,* 1959, 82, 70-77 or later papers referring to this assay). The reduced antibody solution is cooled in an icebath at about 0° C. for 15 minutes; then a solution of about 4.5 equivalents of 1-methyl-3,4-bis(pyridin-2-ylthio)-1H-pyrrole-2,5-dione in dimethylsulfoxide is added and the mixture incubated at 37° C. for 2 hours (or at 4° C. for 20 hours). The resulting modified antibody is purified by size-exclusion chromatography (GE AKTA pure chromatographic system) or PD10 desalting column. A depiction of the described modification is shown in FIG. 12.

Similar syntheses using other disclosed compounds, and/or other antibodies, give the corresponding modified antibody.

Figure 5:
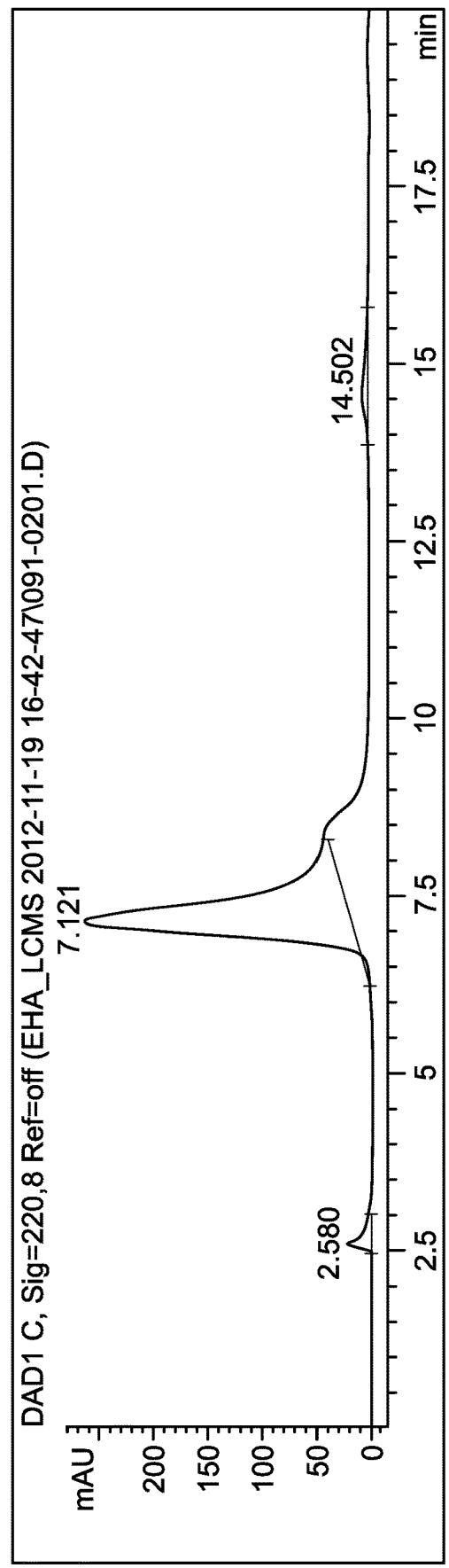
FIG. 5: Antibody Only; RT=7.12
Figure 6:
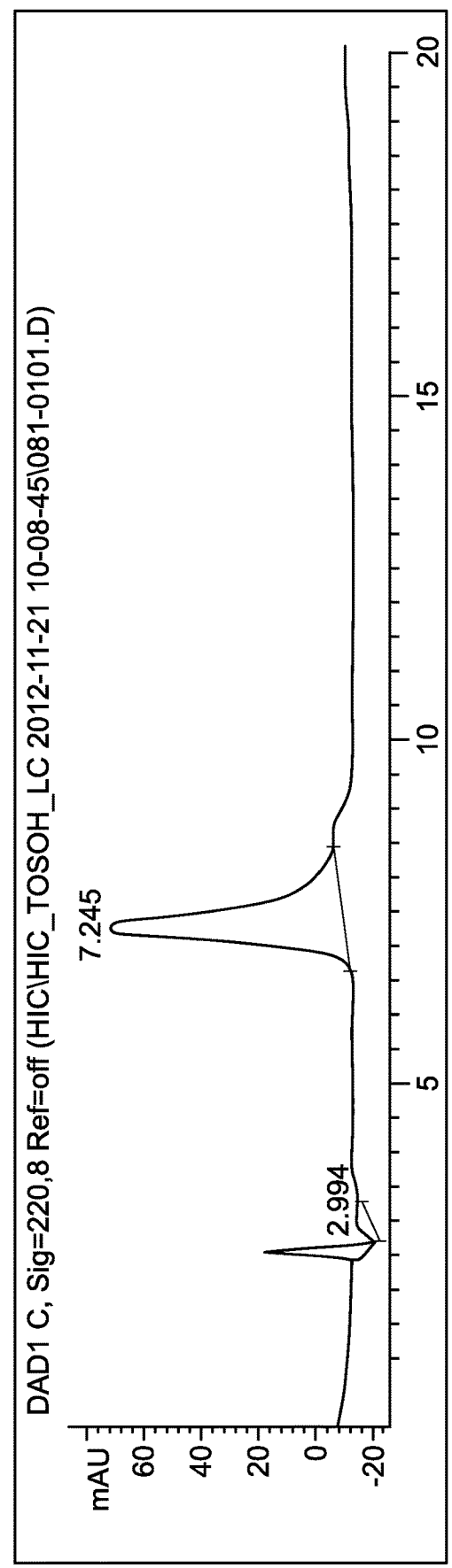
FIG. 6: Antibody+dibromosuccinimide-RT=7.24
Figure 7:
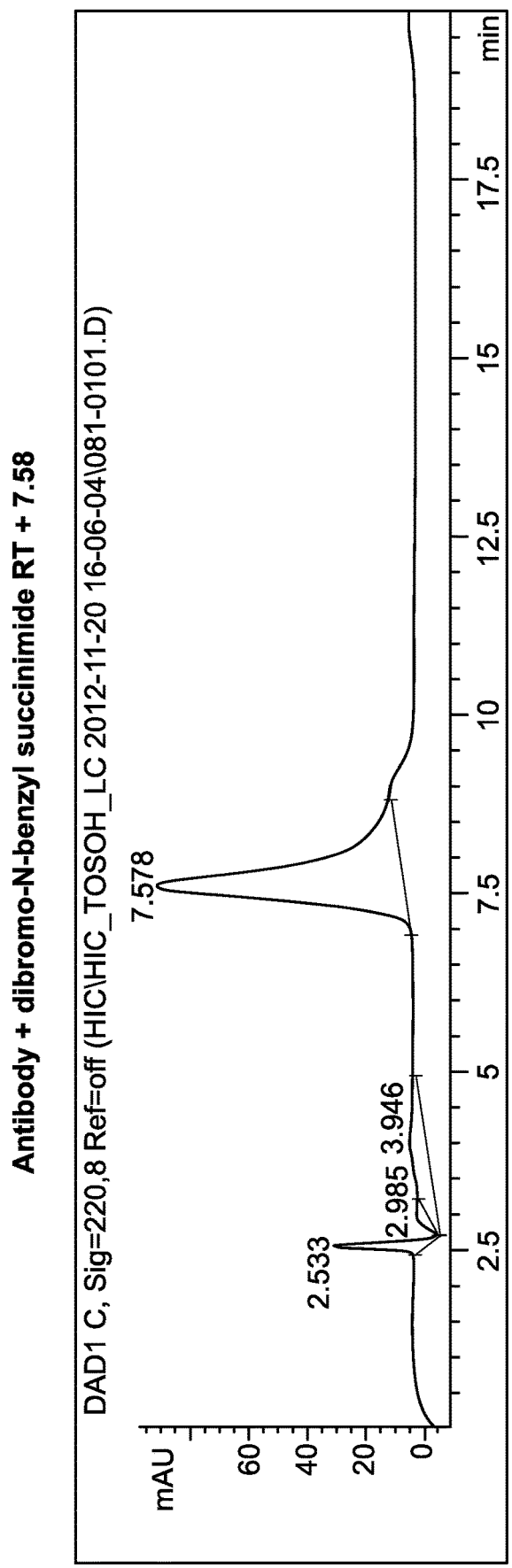
FIG. 7: Antibody+dibromo-N-benzyl succinimide-RT=7.58

As shown in FIGS. 5-7, the modified antibodies prepared from the methods of the present application provide products with significant homogeneity as shown by HIC traces, when compared with modified antibodies prepared by conventional methods that provide inhomogeneous antibodies with multiple products and positional isomers.

Assays

The modified antibodies disclosed herein are tested for potency and selectivity in vitro by determining their activity (e.g., cytotoxicity in cancer cell lines) of interest, such as those cancer cell lines expressing the antigen corresponding to the antibody. The modified antibodies disclosed herein are tested for potency and safety in vivo in animal models of therapeutic efficacy such as the mouse subcutaneous cancer xenograft and mouse orthotopic cancer xenograft models well known to those of skill in the art of cancer research.

Example 4: Binding and Activity of Modified Antibody Compared to Unmodified Antibody The activity of a modified antibody disclosed herein is compared to the activity of the parental antibody (e.g., unmodified) for example, anti-tumor activity in HER2-positive and HER2-negative tumor cells. In certain embodiments, the modified antibodies are as potent and/or stable, or more potent and/or more stable, than their parental (e.g., unmodified) antibodies.

Example 5: Binding Affinity of Modified Antibodies for Antigen-Expressing Cells Binding of the antibodies and modified antibodies to antigen-expressing cells are measured using a cell ELISA. Cells transduced to express the target antigen (e.g., sarcoma cells for HER2, CD98, C10orf54/VISTA) are plated the day at 5000 cells per well in a 384-well plate. The following day, antibodies and modified antibodies are serially diluted in a separate plate, and then transferred to the cell plate, which has previously had media removed by aspiration. After a 2 hour incubation at room temperature, the plate is washed with wash buffer (DPBS at pH7.4 with 0.1% bovine serum albumin) and then 25 pL horseradish peroxidase-labeled secondary antibody diluted in media is added and incubated for 30 minutes at room temperature. The plate is then washed and 15 pL of a chemiluminescent substrate (Pierce catalog #37069) is added; and the plate is read in a plate-based luminescence reader. Antibodies and modified antibodies demonstrating comparable affinity for cells expressing the target antigen indicate that modification does not negatively affect antigen binding.

Example 6: Potency of Modified Antibodies Against Antigen-Expressing Cells

The potency of the modified antibodies disclosed herein for inhibition of tumor cell growth is tested in cell proliferation assays. The Ramos (B-cell lymphoma) Kasumi-3 (acute myeloid leukemia) and BT474 (HER2+ human breast carcinoma) cell lines are seeded into 96 well half-area plates the day before drug treatment at 3000 and 5000 cells per well respectively. Modified antibodies and controls are serially diluted in a master plate, and then transferred to the cell plates, which are incubated at 37° C. and 5% $CO_2$ for 3 days. The cells are quantitated by measuring the level of ATP in the wells using the ATPLitc 1Step kit (Perkin Elmer catalog #50-904-9883) as described by the manufacturer.

Example 7: Efficacy of Modified Antibodies in Murine Xenograft Models

The Ramos cell xenograft model.

The Ramos cell line is obtained from ATCC and cultured according to the supplier's protocols. 4-6 Week-old immunodeficient female mice (Taconic C.B-17 scid) are subcutaneously injected on the right flank with $1\times10^7$ viable cells in a mixture of PBS (without magnesium or calcium) and BD Matrigel (BD Biosciences) at a 1:1 ratio. The injected total volume per mouse is 200 pL with 50% being Matrigel. Once the tumor reaches a size of 65-200 mm 3, mice are randomized. Modified antibodies are formulated in PBS and administered once intravenously at a dose of 1 mg/Kg into the lateral tail vein, and body weights and tumors are measured twice weekly. Tumor volume are calculated as described in van der Horst et al., "Discovery of Fully Human Anti-MET Monoclonal Antibodies with Antitumor Activity against Colon Cancer Tumor Models In vivo", *Neoplasia,* 2009, 11, 355-364. The experiments are performed on groups of 8 animals per experimental point. The negative control group receives HB121 (an IgG2a-negative antibody) at a concentration equimolar to the concentration that would be released by the modified antibody, while the positive control group receives the modified antibody.

The BT474 cell xenograft model.

The BT474 cell line is obtained from ATCC and cultured according to the supplier's protocols. 4-6 Week-old immunodeficient female mice (Taconic C.B-17 scid) are implanted with a [3-estradiol pellet 3 days before being subcutaneously injected on the right flank with $1\times10^7$ viable cells in a mixture of PBS (without magnesium or calcium) and BD Matrigel (BD Biosciences) at a 1:1 ratio. The injected total volume per mouse is 200 pL with 50% being Matrigel. Once the tumor reaches a size of 100-150 $mm^3$, mice are randomized. Modified antibodies are formulated in PBS and administered once intravenously at a dose of 1 mg/Kg into the lateral tail vein, and body weights and tumors are measured twice weekly. Tumor volume is calculated as described in van der Horst et al., cited above. The experiments are performed on groups of 8 animals per experimental point. The negative control group receives HB121 at a concentration equimolar to the concentration that would be released by the modified antibodies, while the positive control group receives trastuzumab at 1 mg/Kg.

Similar tests are conducted with cell lines for other cancers (those expressing different antigens) and modified antibodies where the antibody binds to the antigen expressed by the cancer.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

What is claimed is:

1. A modified antibody represented by the following formula (IIa):

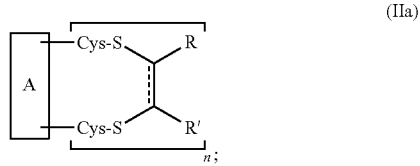

wherein:
A is an antibody or antibody fragment;
the two depicted cysteine residues are from at least one reduced interchain cysteine-cysteine disulfide bond in A;
n is an integer from 1 to 13;
the ══ bond represents a single or a double bond; and
each R and R' is independently hydrogen or $C_{1-6}$ alkyl, wherein one or more carbons in the $C_{1-6}$ alkyl are optionally substituted by a group selected from an oxo, a thio, an imine, and a substituted imine.

2. The modified antibody of claim 1, wherein the modified antibody is represented by the following formula (IId):

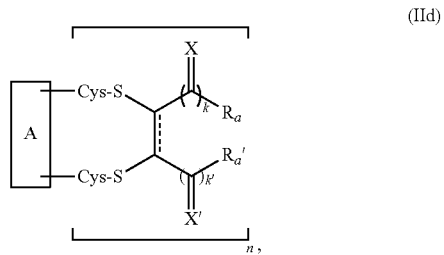

wherein:
each $R_a$ and $R_a'$ is independently hydrogen, $C_{1-3}$alkyl, or absent.

3. The modified antibody of claim 1, wherein the ══ bond represents a single bond.

4. The modified antibody of claim 1, wherein n is 4.

5. The modified antibody of claim 1, wherein A is an antibody that is specific to a cancer antigen.

6. The modified antibody of claim 1, wherein A is selected from the group consisting of alemtuzumab, anitumumab, bevacizumab, brentuximab, cetuximab, gemtuzumab, glembatumumab, inotuzumab, ipilimumab, lovortumumab, milatuzumab, ofatumumab, rituximab, tositumomab, and trastuzumab.

* * * * *